US012564623B2

(12) United States Patent (10) Patent No.: US 12,564,623 B2
Becker et al. (45) Date of Patent: Mar. 3, 2026

(54) METHODS AND COMPOSITIONS FOR TREATING CANCER

(71) Applicant: The University of Chicago, Chicago, IL (US)

(72) Inventors: Lev Becker, Chicago, IL (US); Chang Cui, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1307 days.

(21) Appl. No.: 16/621,549

(22) PCT Filed: Jun. 15, 2018

(86) PCT No.: PCT/US2018/037800
§ 371 (c)(1),
(2) Date: Sep. 24, 2021

(87) PCT Pub. No.: WO2018/232273
PCT Pub. Date: Dec. 20, 2018

(65) Prior Publication Data
US 2021/0299234 A1 Sep. 30, 2021

Related U.S. Application Data

(60) Provisional application No. 62/610,711, filed on Dec. 27, 2017, provisional application No. 62/520,325, filed on Jun. 15, 2017.

(51) Int. Cl.
*A61K 38/54* (2006.01)
*A61K 38/46* (2006.01)
*A61K 38/48* (2006.01)

(52) U.S. Cl.
CPC ............ *A61K 38/54* (2013.01); *A61K 38/465* (2013.01); *A61K 38/48* (2013.01); *C12Y 301/26003* (2013.01); *C12Y 304/21037* (2013.01)

(58) Field of Classification Search
CPC .... C12Y 304/21037; C12Y 304/21036; A61K 38/54
See application file for complete search history.

(56) References Cited

U.S. PATENT DOCUMENTS

| | | | |
|---|---|---|---|
| 5,698,518 | A | 12/1997 | Carson et al. |
| 2005/0257285 | A1 | 11/2005 | Gupta |
| 2006/0008891 | A1 | 1/2006 | Wang et al. |
| 2006/0019256 | A1 | 1/2006 | Clarke et al. |
| 2006/0045881 | A1 | 3/2006 | Modrem |
| 2006/0177880 | A1 | 8/2006 | Tacke et al. |
| 2007/0161125 | A1 | 7/2007 | Rosenfeld et al. |
| 2009/0162343 | A1* | 6/2009 | Franano ................... A61P 9/00 |
| | | | 435/254.11 |
| 2011/0151490 | A1 | 6/2011 | Hillman et al. |

FOREIGN PATENT DOCUMENTS

| | | | |
|---|---|---|---|
| JP | 2004-123679 | 4/2004 | |
| JP | 2006-500944 | 1/2006 | |
| WO | WO 1992/002617 | 2/1992 | |
| WO | WO-03083084 A2 * | 10/2003 | ............ C07K 14/47 |
| WO | WO 2004/031409 | 4/2004 | |
| WO | WO 2016125330 | 8/2016 | |

OTHER PUBLICATIONS

Marcus E Peter (2014) DICE, Cell Cycle, 13:9, 1373-1378. (Year: 2014).*
C. Lee Ventola (2017), P&T, vol. 42 No. 8, pp. 514-521. (Year: 2014).*
The Jackson Laboratory, Say goodbye to one size fits all cancer treatments, pp. 1-3,. (Year: 2018).*
Uniprot, P00772 CELA1_PIG, 99. 1-7, retrieved from https://www.uniprot.org/uniprotkb/P00772/entry, accessed on Sep. 19, 2025. (Year: 2025).*
Extended European Search Report issued in Corresponding European Application No. 18817894.1, dated Feb. 5, 2021.
Ho et al., "Neutrophil elastase as a diagnostic marker and therapeutic target in colorectal cancers" Oncotarget 2014, 5(2), 473-480.
Albrethsen et al., "Upregulated expression of human neutrophil peptides 1, 2 and 3 (HNP 1-3) in colon cancer serum and tumours: a biomarker study" BMC Cancer 2005, 5(8), 10 pages.
Cao et al., "Potential roles of eosinophils in cancer therapy: epidemiological studies, experimental models, and clinical pathology" Recent Pat Anticancer Drug Discov. 2014, 9(2), 1-8.
Chang et al., "TNF-alpha mediates eosinophil cationic protein-induced apoptosis in BEAS-2B cells" BMC Cell Biol. 2010, 11(6), 14 pages.
Chen et al., "CD95 promotes tumour growth" Nature 465, 492-496.
Coffelt et al., "Neutrophils in cancer: neutral no more" Nature Reviews Cancer 2016, 16, 431-446.
De Lima et al., "Effect of eosinophil cationic protein on human oral squamous carcinoma cell viability" Molecular and Clinical Oncology 2015, 3, 353-356.
Eruslanov et al., "Tumor-associated neutrophils stimulate T cell responses in early-stage human lung cancer" The Journal of Clinical Investigation 2014, 34 pages.

(Continued)

*Primary Examiner* — Lianko G Garyu
*Assistant Examiner* — Claudia Espinosa
(74) *Attorney, Agent, or Firm* — Norton Rose Fulbright US LLP

(57) ABSTRACT

Embodiments are directed to: (i) neutrophil secreted factors that have the capacity to kill a broad range of cancer cells without affecting the viability of non-cancer cells. Two neutrophil killing factors have been identified by the inventors: (1) eosinophil cationic protein (ECP) and (2) neutrophil elastase (ELANE); or (ii) therapeutic compositions that include CD95 degrading polypeptide components and methods of treating cancer with the same.

7 Claims, 21 Drawing Sheets

Specification includes a Sequence Listing.

(56) References Cited

OTHER PUBLICATIONS

Fox et al., "Neutrophil Apoptosis: Relevance to the Innate Immune Response and Inflammatory Disease" *Journal of Innate Immunity* 2010, 2, 216-227.

Hadji et al., "Death Induced by CD95 or CD95 Ligand Elimination" *Cell Rep.* 2014, 7(1), 208-222.

Holterman et al., "Overexpression of alpha-defensin is associated with bladder cancer invasiveness" *Urol Oncol.* 2006, 24(2), 97-108.

Hunt et al., "Elafin, an inhibitor of elastase, is a prognostic indicator in breast cancer" *Breast Cancer Res.* 2013, 15(1), 13 pages.

International Search Report and Written Opinion in corresponding application No. PCT/US2018/037800, dated Jun. 15, 2018.

Kopolovic et al., "A systematic review of transfusion-associated graft-versus-host disease" *Blood* 2015, 126(3), 406-414.

Loison et al., "Proteinase 3-dependent caspase-3 cleavage modulates neutrophil death and inflammation" *J Clin Invest* 2014, 124(10), 4445-4458.

Martin-Villalba et al., "CD95 in cancer: tool or target?" *Trends in Molecular Medicine* 2013, 19(6), 329-335.

Mishalian et al., "Tumor-associated neutrophils (TAN) develop pro-tumorigenic properties during tumor progression." *Cancer Immunol Immunother.* 2013, 62(11), 1745-1756.

Murmann et al., "Induction of DISE in ovarian cancer cells in vivo" *Oncotarget* 2017, 8(49), 84643-84658.

Peter, "DICE: A novel tumor surveillance mechanism—a new therapy for cancer?" *Cell Cycle* 2014, 13(9), 1373-1378.

Putzbach et al., "Many si/shRNAs can kill cancer cells by targeting multiple survival genes through an off-target mechanism" *eLife* 2017, 6, 43 pages.

Qi et al., "Role of annexin A6 in cancer" Oncol Lett. 2015, 10(4), 1947-1952.

Sato et al., "Neutrophil elastase and cancer" *Surg Oncol.* 2006, 15(4), 217-222.

Vilá de Muga et al., "Annexin A6 inhibits Ras signalling in breast cancer cells" *Oncogene.* 2009, 28(3), 363-377.

Wada et al., "Neutrophil elastase induces cell proliferation and migration by the release of TGF-alpha, PDGF and VEGF in esophageal cell lines" *Oncol Rep.* 2007, 17(1), 161-167.

Wada et al., "Sivelestat, a specific neutrophil elastase inhibitor, suppresses the growth of gastric carcinoma cells by preventing the release of transforming growth factor-alpha" *Cancer Sci.* 2006, 97(10), 1037-1043.

Wang et al., "Annexin A6 is down-regulated through promoter methylation in gastric cancer" *Am J Transl Res.* 2013, 5 (5), 555-562.

Winter et al., "Human Defensins: Potential Tools for Clinical Applications" *Polymers* 2012, 4, 691-709.

Xu et al., "Human alpha-defensin-1 inhibits growth of human lung adenocarcinoma xenograft in nude mice" *Mol Cancer Ther.* 2008, 7(6), 1588-1597.

Young et al., "Mechanism of membrane damage mediated by human eosinophil cationic protein" *Nature* 1986, 321, 613-616.

Zalewski et al., "Apoptosis-Regulatory Factors as Potential Drug Targets in the Epithelium of Normal and Inflamed Airways" *Current Molecular Pharmacology* 2008, 1, 38-49.

Office Action issued in Corresponding Japanese Application No. 2019-569454, dated May 9, 2022 (English Translation provided).

English translation of Office Communication issued in Japanese Patent Application No. 2022-192891, dated Jan. 30, 2024.

* cited by examiner

*FIG. 21A-D*
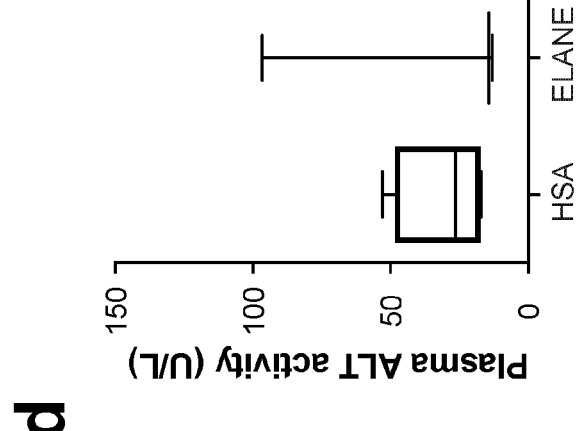
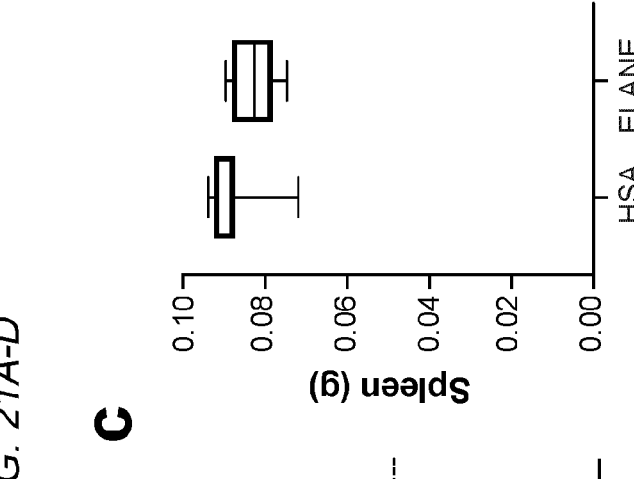
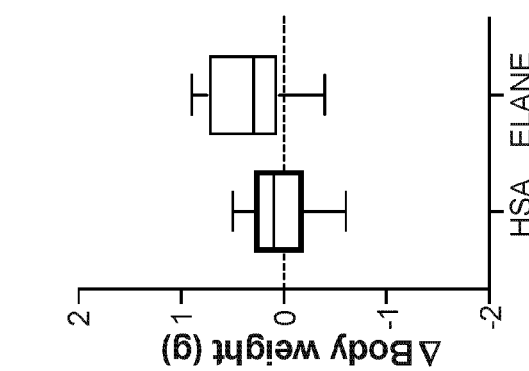
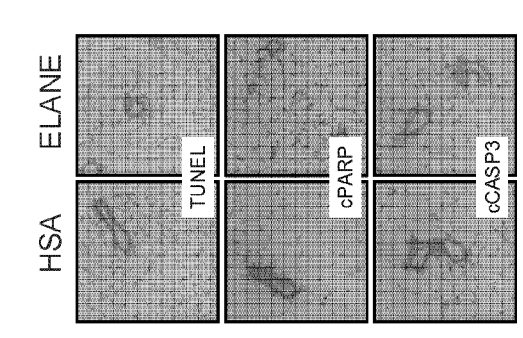

SEQUENCE LISTING

<160> NUMBER OF SEQ ID NOS: 8

<210> SEQ ID NO 1
<211> LENGTH: 160
<212> TYPE: PRT
<213> ORGANISM: Homo sapiens

<400> SEQUENCE: 1

```
Met Val Pro Lys Leu Phe Thr Ser Gln Ile Cys Leu Leu Leu Leu Leu
1               5                   10                  15

Gly Leu Met Gly Val Glu Gly Ser Leu His Ala Arg Pro Pro Gln Phe
            20                  25                  30

Thr Arg Ala Gln Trp Phe Ala Ile Gln His Ile Ser Leu Asn Pro Pro
        35                  40                  45

Arg Cys Thr Ile Ala Met Arg Ala Ile Asn Asn Tyr Arg Trp Arg Cys
    50                  55                  60

Lys Asn Gln Asn Thr Phe Leu Arg Thr Thr Phe Ala Asn Val Val Asn
65                  70                  75                  80

Val Cys Gly Asn Gln Ser Ile Arg Cys Pro His Asn Arg Thr Leu Asn
                85                  90                  95

Asn Cys His Arg Ser Arg Phe Arg Val Pro Leu Leu His Cys Asp Leu
            100                 105                 110

Ile Asn Pro Gly Ala Gln Asn Ile Ser Asn Cys Thr Tyr Ala Asp Arg
            115                 120                 125

Pro Gly Arg Arg Phe Tyr Val Val Ala Cys Asp Asn Arg Asp Pro Arg
        130                 135                 140

Asp Ser Pro Arg Tyr Pro Val Val Pro Val His Leu Asp Thr Thr Ile
145                 150                 155                 160
```

<210> SEQ ID NO 2
<211> LENGTH: 267
<212> TYPE: PRT
<213> ORGANISM: Homo sapiens

<400> SEQUENCE: 2

```
Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
        130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
```

```
                      165                  170                  175

Val Thr Ser Leu Cys Arg Arg Ser Asn Val Cys Thr Leu Val Arg Gly
            180                  185                  190

Arg Gln Ala Gly Val Cys Phe Gly Asp Ser Gly Ser Pro Leu Val Cys
        195                  200                  205

Asn Gly Leu Ile His Gly Ile Ala Ser Phe Val Arg Gly Gly Cys Ala
        210                  215                  220

Ser Gly Leu Tyr Pro Asp Ala Phe Ala Pro Val Ala Gln Phe Val Asn
225                  230                  235                  240

Trp Ile Asp Ser Ile Ile Gln Arg Ser Glu Asp Asn Pro Cys Pro His
                245                  250                  255

Pro Arg Asp Pro Asp Pro Ala Ser Arg Thr His
                260                  265

<210> SEQ ID NO 3
<211> LENGTH: 255
<212> TYPE: PRT
<213> ORGANISM: Homo sapiens

<400> SEQUENCE: 3

Met Gln Pro Leu Leu Leu Leu Leu Ala Phe Leu Leu Pro Thr Gly Ala
1                   5                   10                  15

Glu Ala Gly Glu Ile Ile Gly Gly Arg Glu Ser Arg Pro His Ser Arg
                20                  25                  30

Pro Tyr Met Ala Tyr Leu Gln Ile Gln Ser Pro Ala Gly Gln Ser Arg
            35                  40                  45

Cys Gly Gly Phe Leu Val Arg Glu Asp Phe Val Leu Thr Ala Ala His
        50                  55                  60

Cys Trp Gly Ser Asn Ile Asn Val Thr Leu Gly Ala His Asn Ile Gln
65                  70                  75                  80

Arg Arg Glu Asn Thr Gln Gln His Ile Thr Ala Arg Arg Ala Ile Arg
                85                  90                  95

His Pro Gln Tyr Asn Gln Arg Thr Ile Gln Asn Asp Ile Met Leu Leu
            100                 105                 110

Gln Leu Ser Arg Arg Val Arg Arg Asn Arg Asn Val Asn Pro Val Ala
        115                 120                 125

Leu Pro Arg Ala Gln Glu Gly Leu Arg Pro Gly Thr Leu Cys Thr Val
        130                 135                 140

Ala Gly Trp Gly Arg Val Ser Met Arg Arg Gly Thr Asp Thr Leu Arg
145                 150                 155                 160

Glu Val Gln Leu Arg Val Gln Arg Asp Arg Gln Cys Leu Arg Ile Phe
                165                 170                 175

Gly Ser Tyr Asp Pro Arg Arg Gln Ile Cys Val Gly Asp Arg Arg Glu
            180                 185                 190

Arg Lys Ala Ala Phe Lys Gly Asp Ser Gly Gly Pro Leu Leu Cys Asn
        195                 200                 205

Asn Val Ala His Gly Ile Val Ser Tyr Gly Lys Ser Ser Gly Val Pro
        210                 215                 220

Pro Glu Val Phe Thr Arg Val Ser Ser Phe Leu Pro Trp Ile Arg Thr
225                 230                 235                 240

Thr Met Arg Ser Phe Lys Leu Leu Asp Gln Met Glu Thr Pro Leu
                245                 250                 255

<210> SEQ ID NO 4
<211> LENGTH: 256
```

```
<212> TYPE: PRT
<213> ORGANISM: Homo sapiens

<400> SEQUENCE: 4

Met Ala His Arg Pro Pro Ser Pro Ala Leu Ala Ser Val Leu Leu Ala
1               5                   10                  15

Leu Leu Leu Ser Gly Ala Ala Arg Ala Ala Glu Ile Val Gly Gly His
            20                  25                  30

Glu Ala Gln Pro His Ser Arg Pro Tyr Met Ala Ser Leu Gln Met Arg
        35                  40                  45

Gly Asn Pro Gly Ser His Phe Cys Gly Gly Thr Leu Ile His Pro Ser
    50                  55                  60

Phe Val Leu Thr Ala Ala His Cys Leu Arg Asp Ile Pro Gln Arg Leu
65                  70                  75                  80

Val Asn Val Val Leu Gly Ala His Asn Val Arg Thr Gln Glu Pro Thr
                85                  90                  95

Gln Gln His Phe Ser Val Ala Gln Val Phe Leu Asn Asn Tyr Asp Ala
            100                 105                 110

Glu Asn Lys Leu Asn Asp Val Leu Leu Ile Gln Leu Ser Ser Pro Ala
        115                 120                 125

Asn Leu Ser Ala Ser Val Ala Thr Val Gln Leu Pro Gln Gln Asp Gln
    130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
            180                 185                 190

Arg Arg Lys Ala Gly Ile Cys Phe Gly Asp Ser Gly Gly Pro Leu Ile
        195                 200                 205

Cys Asp Gly Ile Ile Gln Gly Ile Asp Ser Phe Val Ile Trp Gly Cys
    210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255

<210> SEQ ID NO 5
<211> LENGTH: 265
<212> TYPE: PRT
<213> ORGANISM: Mus musculus

<400> SEQUENCE: 5

Met Ala Leu Gly Arg Leu Ser Ser Arg Thr Leu Ala Ala Met Leu Leu
1               5                   10                  15

Ala Leu Phe Leu Gly Gly Pro Ala Leu Ala Ser Glu Ile Val Gly Gly
            20                  25                  30

Arg Pro Ala Arg Pro His Ala Trp Pro Phe Met Ala Ser Leu Gln Arg
        35                  40                  45

Arg Gly Gly His Phe Cys Gly Ala Thr Leu Ile Ala Arg Asn Phe Val
    50                  55                  60

Met Ser Ala Ala His Cys Val Asn Gly Leu Asn Phe Arg Ser Val Gln
65                  70                  75                  80

Val Val Leu Gly Ala His Asp Leu Arg Arg Gln Glu Arg Thr Arg Gln
                85                  90                  95
```

-continued

```
Thr Phe Ser Val Gln Arg Ile Phe Glu Asn Gly Phe Asp Pro Ser Gln
                100                 105                 110

Leu Leu Asn Asp Ile Val Ile Ile Gln Leu Asn Gly Ser Ala Thr Ile
            115                 120                 125

Asn Ala Asn Val Gln Val Ala Gln Leu Pro Ala Gln Gly Gln Gly Val
        130                 135                 140

Gly Asp Arg Thr Pro Cys Leu Ala Met Gly Trp Gly Arg Leu Gly Thr
145                 150                 155                 160

Asn Arg Pro Ser Pro Ser Val Leu Gln Glu Leu Asn Val Thr Val Val
                165                 170                 175

Thr Asn Met Cys Arg Arg Arg Val Asn Val Cys Thr Leu Val Pro Arg
            180                 185                 190

Arg Gln Ala Gly Ile Cys Phe Gly Asp Ser Gly Gly Pro Leu Val Cys
        195                 200                 205

Asn Asn Leu Val Gln Gly Ile Asp Ser Phe Ile Arg Gly Gly Cys Gly
    210                 215                 220

Ser Gly Leu Tyr Pro Asp Ala Phe Ala Pro Val Ala Glu Phe Ala Asp
225                 230                 235                 240

Trp Ile Asn Ser Ile Ile Arg Ser His Asn Asp His Leu Leu Thr His
                245                 250                 255

Pro Lys Asp Arg Glu Gly Arg Thr Asn
                260                 265

<210> SEQ ID NO 6
<211> LENGTH: 266
<212> TYPE: PRT
<213> ORGANISM: Sus scrofa

<400> SEQUENCE: 6

Met Leu Arg Leu Leu Val Val Ala Ser Leu Val Leu Tyr Gly His Ser
1               5                   10                  15

Thr Gln Asp Phe Pro Glu Thr Asn Ala Arg Val Val Gly Gly Thr Glu
            20                  25                  30

Ala Gln Arg Asn Ser Trp Pro Ser Gln Ile Ser Leu Gln Tyr Arg Ser
        35                  40                  45

Gly Ser Ser Trp Ala His Thr Cys Gly Gly Thr Leu Ile Arg Gln Asn
    50                  55                  60

Trp Val Met Thr Ala Ala His Cys Val Asp Arg Glu Leu Thr Phe Arg
65                  70                  75                  80

Val Val Val Gly Glu His Asn Leu Asn Gln Asn Asp Gly Thr Glu Gln
                85                  90                  95

Tyr Val Gly Val Gln Lys Ile Val Val His Pro Tyr Trp Asn Thr Asp
                100                 105                 110

Asp Val Ala Ala Gly Tyr Asp Ile Ala Leu Leu Arg Leu Ala Gln Ser
            115                 120                 125

Val Thr Leu Asn Ser Tyr Val Gln Leu Gly Val Leu Pro Arg Ala Gly
        130                 135                 140

Thr Ile Leu Ala Asn Asn Ser Pro Cys Tyr Ile Thr Gly Trp Gly Leu
145                 150                 155                 160

Thr Arg Thr Asn Gly Gln Leu Ala Gln Thr Leu Gln Gln Ala Tyr Leu
                165                 170                 175

Pro Thr Val Asp Tyr Ala Ile Cys Ser Ser Ser Ser Tyr Trp Gly Ser
            180                 185                 190

Thr Val Lys Asn Ser Met Val Cys Ala Gly Gly Asp Gly Val Arg Ser
        195                 200                 205
```

Gly Cys Gln Gly Asp Ser Gly Gly Pro Leu His Cys Leu Val Asn Gly
    210                 215                 220

Gln Tyr Ala Val His Gly Val Thr Ser Phe Val Ser Arg Leu Gly Cys
225                 230                 235                 240

Asn Val Thr Arg Lys Pro Thr Val Phe Thr Arg Val Ser Ala Tyr Ile
                245                 250                 255

Ser Trp Ile Asn Asn Val Ile Ala Ser Asn
            260                 265

<210> SEQ ID NO 7
<211> LENGTH: 266
<212> TYPE: PRT
<213> ORGANISM: Mus musculus

<400> SEQUENCE: 7

Met Leu Arg Phe Leu Val Phe Ala Ser Leu Val Leu Cys Gly His Ser
1                 5                  10                  15

Thr Glu Asp Val Pro Glu Thr Asp Ala Arg Val Val Gly Gly Ala Glu
                20                  25                  30

Ala Arg Arg Asn Ser Trp Pro Ser Gln Ile Ser Leu Gln Tyr Gln Tyr
            35                  40                  45

Gly Gly Ser Trp His His Thr Cys Gly Gly Thr Leu Ile Arg Ser Asn
        50                  55                  60

Trp Val Met Thr Ala Ala His Cys Val Asp Ser Pro Met Thr Tyr Arg
65                  70                  75                  80

Val Val Val Gly Glu His Asn Leu Ser Gln Asn Asp Gly Thr Glu Gln
                85                  90                  95

Tyr Val Asn Val Gln Lys Ile Val Ser His Pro Tyr Trp Asn Lys Asn
                100                 105                 110

Asn Val Val Ala Gly Tyr Asp Ile Ala Leu Leu Arg Leu Ala Lys Ser
            115                 120                 125

Val Thr Leu Asn Asn Tyr Val Gln Leu Gly Val Leu Pro Arg Glu Gly
    130                 135                 140

Thr Ile Leu Ala Asn Asn Ser Pro Cys Tyr Ile Thr Gly Trp Gly Arg
145                 150                 155                 160

Thr Arg Thr Asn Gly Glu Leu Ala Gln Thr Leu Gln Gln Ala Tyr Leu
                165                 170                 175

Pro Ser Val Ser Tyr Ser Ile Cys Ser Ser Ser Ser Tyr Trp Gly Ser
            180                 185                 190

Ser Val Lys Asn Thr Met Val Cys Ala Gly Gly Asp Gly Val Arg Ser
            195                 200                 205

Gly Cys Gln Gly Asp Ser Gly Gly Pro Leu His Cys Met Val Asn Gly
    210                 215                 220

Gln Tyr Ala Val His Gly Val Thr Ser Phe Val Ser Ser Met Gly Cys
225                 230                 235                 240

Asn Val Ala Arg Lys Pro Thr Val Phe Thr Arg Val Ser Ala Tyr Ile
                245                 250                 255

Ser Trp Met Asn Asn Val Ile Ala Ser Asn
            260                 265

<210> SEQ ID NO 8
<211> LENGTH: 269
<212> TYPE: PRT
<213> ORGANISM: Rattus norvegicus

<400> SEQUENCE: 8

-continued

```
Met Leu Arg Phe Leu Val Phe Ala Ser Leu Val Leu Tyr Gly His Ser
1               5                   10                  15

Thr Gln Asp Phe Pro Glu Thr Asn Ala Arg Val Val Gly Gly Ala Glu
            20                  25                  30

Ala Arg Arg Asn Ser Trp Pro Ser Gln Ile Ser Leu Gln Tyr Leu Ser
        35                  40                  45

Gly Gly Ser Trp Tyr His Thr Cys Gly Gly Thr Leu Ile Arg Arg Asn
    50                  55                  60

Trp Val Met Thr Ala Ala His Cys Val Ser Ser Gln Met Thr Phe Arg
65                  70                  75                  80

Val Val Val Gly Asp His Asn Leu Ser Gln Asn Asp Gly Thr Glu Gln
                85                  90                  95

Tyr Val Ser Val Gln Lys Ile Val Val His Pro Asn Trp Asn Ser Asn
            100                 105                 110

Asn Val Ala Ala Gly Tyr Asp Ile Ala Leu Leu Arg Leu Ala Gln Ser
            115                 120                 125

Val Thr Leu Asn Asn Tyr Val Gln Leu Ala Val Leu Pro Gln Glu Gly
    130                 135                 140

Thr Ile Leu Ala Asn Asn Asn Pro Cys Tyr Ile Thr Gly Trp Gly Arg
145                 150                 155                 160

Thr Arg Thr Asn Gly Gln Leu Ser Gln Thr Leu Gln Gln Ala Tyr Leu
            165                 170                 175

Pro Ser Val Asp Tyr Ser Ile Cys Ser Ser Ser Ser Tyr Trp Gly Ser
            180                 185                 190

Thr Val Lys Thr Thr Met Val Cys Ala Gly Gly Asp Gly Val Arg Ser
            195                 200                 205

Gly Cys Gln Gly Asp Ser Gly Gly Pro Leu His Cys Leu Val Asn Gly
    210                 215                 220

Gln Tyr Ser Val His Gly Val Thr Ser Phe Val Ser Ser Met Gly Cys
225                 230                 235                 240

Asn Val Ser Arg Lys Pro Thr Val Phe Thr Arg Val Ser Ala Tyr Ile
            245                 250                 255

Ser Trp Met Asn Asn Val Ile Ala Tyr Asn Ser Glu Gln
            260                 265
```

METHODS AND COMPOSITIONS FOR TREATING CANCER

CROSS-REFERENCE TO RELATED APPLICATIONS

This application is a national phase application under 35 U.S.C. § 371 of International Application No. PCT/US2018/037800 filed Jun. 15, 2018, which claims priority to U.S. Provisional Patent Application Nos. 62/520,325 filed Jun. 15, 2017 and 62/610,711 filed Dec. 27, 2017, all of which are incorporated herein by reference in their entireties.

FIELD OF THE INVENTION

Certain embodiments are directed generally to biology, medicine, and cancer therapy. Certain aspects are directed to protein compositions having a protein or polypeptide component that is toxic to a variety of cancer cells. Other aspects are directed to protein compositions having or delivering a protein or polypeptide component that degrades CD95.

BACKGROUND

Precision medicine, medical care designed to optimize efficiency or therapeutic benefit for particular groups of patients by using genetic or molecular profiling, has gained tremendous traction for treating cancer. Identifying the specific genomic abnormalities that (i) confer risk of developing cancer, (ii) influence tumor growth, and (iii) regulate metastasis have defined how cancer is diagnosed, determined how targeted therapies are developed and implemented, and shaped cancer prevention strategies.

The need for precision medicine in cancer is largely based on the failure to identify targetable properties in tumor cells that distinguish them from healthy, non-cancer cells. Indeed, although radiation and/or chemotherapies have the capacity to effectively kill many if not most cancer cells, their efficacy is severely limited by cytotoxic effects on non-cancer cells. These findings demonstrate that rapid cell division, a property targeted by radiation therapy and chemotherapy, is not unique enough to cancer cells to achieve the specificity required to limit extensive side effects.

CD95 (FAS/APO-1/TNFRSF6) is a cell surface receptor that triggers apoptosis through multiple mechanisms. Through the traditional mechanism, FAS ligand (FASL/CD95L) binding to CD95 induces its death domain (DD) to recruit a number of factors, including the adaptor molecule FADD, procaspase-8/10, and the caspase-8/10 regulator c-FLIP. The formation of a death-inducing signaling complex (DISC) results in autoproteolytic processing and activation of caspase-8, which directly or indirectly activates caspase-3 to induce apoptosis (Peter and Krammer, Cell Death Differ., 2003).

Although there has been considerable interest in using FASL to trigger CD95-mediated apoptosis to treat cancer, this approach has encountered two important roadblocks. First, CD95 is ubiquitously expressed throughout the body, with particularly abundant expression in the thymus, liver, heart, and kidney. Thus, attempts to kill cancer cells by delivering FASL have been thwarted by the induction of apoptosis in healthy non-cancer cells, such as hepatocytes, resulting in acute hepatic necrosis (Bidere et al., *Annu. Rev. Immunol.,* 2006). Second, tumor cells have multiple ways to become resistant to CD95/CD95L-mediated apoptosis (Al-geciras-Schimnich et al., *Proc Natl Acad Sci USA.,* 2003; Ivanov et al., *Mol Cell Biol.,* 2003, Ivanov et al., *J Biol*

*Chem.,* 2006). In addition, these resistant tumor cells can actually overexpress FASL to kill infiltrating T-cells, in an effort to evade the immune system (O'Connell et al. *J. Exp. Med.,* 1996).

More recent studies have shown that CD95 can also trigger cancer cell apoptosis through a second mechanism that is independent of the FASL-mediated pathway (Chen et al., *Nature.,* 2010; Hadji et al., Cell Rep., 2014). These studies showed that CD95 knockdown by siRNA or shRNA induced tumor cell apoptosis in multiple cancer cell lines, through a pathway referred to as 'death induced by CD95R/L elimination' (DICE). DICE induces apoptosis in cancer cells by a pathway involving cell swelling, reactive oxygen species (ROS) production, followed by DNA damage, activation of caspases, and loss of mitochondrial outer membrane permeabilization (MOMP). Genetic deletion of CD95 in liver or ovarian cancer cells induced apoptosis in mice, resulting in immune cell infiltration and profound reduction in cancer progression. In contrast, CD95 knockout (Cd95-/-) mice did not show signs of cell death or growth deficiencies in normal non-tumor bearing mice, apart from T-cell depletion, suggesting that DICE preferentially affects cancer cells with little effect on normal cells (outside of immune system) (Adachi et al., *Nat. Genet.,* 1995; Karray et al., *J. Immunol.,* 2004).

These findings suggest that delivering siRNA or shRNA to lower CD95 levels in tumor cells may be a viable approach for the treatment of cancer. However, there are two important problems with this strategy. First, significant barriers still exist to implementing siRNA drugs for cancer therapy, including poor cellular uptake, instability under physiological conditions, off-target effects, and possible immunogenicity (Dominska and Dykxhoorn., *J Cell Sci.,* 2010; Jackson and Linsley et al., *Nat Rev Drug Discov.,* 2010; Moschos et al., *Bioconjug Chem.,* 2007). Second, because CD95 is essential for T-cell survival, proliferation, and activation, deleting CD95 in T cells causes lymphopenia in mice (Hao et al., *J. Exp. Med.,* 2004; Krammer., *Nature,* 2000), this approach may produce unwanted side effects by depleting T-cells and inhibiting anti-tumor immunity.

There is a need for additional methods and compositions for broad based cancer specific therapies that are minimally toxic to non-cancer cells and tissues and have minimal or no long term negative side effects.

SUMMARY

One solution to the off-target cancer therapy toxicity problem is the development of targeted cancer therapies that have the capability to kill cancer cells leaving healthy cells intact by identifying targets in cancer cells that differentiate it from healthy cells. One method of targeted therapy is the use of anti-cancer molecules that are capable of targeting cancer cells. These molecules could be isolated from cells and/or be synthetically manufactured. These cancer-killing molecules can also be used in combination with radiotherapy, chemotherapy, immunotherapy, targeted therapy, or anti-hormone therapy to improve the effectiveness of cancer killing. One source of such targeted cancer killing molecules is neutrophils. The inventors have discovered neutrophil secreted factors that have the capacity to kill a broad range of cancer cells. In certain aspects the factors minimally affect the viability of non-cancer cells and have minimal to no negative side effects.

Embodiments use a therapeutic polypeptide (anti-cancer agent) composition in place of cell based therapies. The therapeutic compositions described herein are advantageous over neutrophils and/or neutrophil stimulating or recruiting agents for at least three reasons: (1) By delivering the anticancer agents (i.e., polypeptide composition described herein) as described herein one has better control over dosing regimens and can therefore better modulate efficacy and potential toxicity of the therapeutic. (2) Substantial evidence suggests that tumors can reprogram the anti-tumor neutrophils in early stage cancer to a pro-tumor phenotype and thus promote metastasis (Eruslanov et al., 2014; Mishalian et al., 2013; Coffelt et al., 2016). Thus, there is a potential for tumors to block the ability of delivered neutrophils to release anti-cancer agents, or even worse, to stimulate production of pro-tumorigenic factors. (3) Keeping neutrophils alive before the transfusion as well as the Graft-versus-Host disease following the transfusion of leukocytes are currently a challenge (Kopolovic et al., 2015; Fox et al., 2010).

Two neutrophil secreted factors have been identified by the inventors: (1) eosinophil cationic protein (ECP), and (2) neutrophil elastase (ELANE). The inventors have determined that these components and variants thereof have a cancer specific killing capability, which can be enhanced by various combinations of these factors.

In certain aspects eosinophil cationic protein (ECP) or variant thereof has an amino acid sequence that is 90, 92, 94, 96, 98, 99, to 100% identical, including all values and ranges there between, over 50, 60, 70, 80, 90, 100, 110, 120, 130, 140, 150, or 155 contiguous amino acids, including all values and ranges there between, to MVPKLFTSQI-CLLLLLG LMGVEGSLHARPPQFTRAQWFAIQHIS-LNPPRCTIAMRAINNYRWRCKNQNTFLRTT FANVVNVCGNQSIRCPHNRTLNNCHRSRFR VPLLHCDLINPGAQNISNCTYADRPGR RFYV-VACDNRDPRDSPRYPVVPVHLDTTI (SEQ ID NO:1). Other aspects are directed to an ECP polypeptide or variant thereof having 50, 60, 70, 80, 90, 100, 110, 120, 130, 140, 150, or 155 contiguous amino acids of the ECP polypeptide that is 90, 92, 94, 69, 98, 99, to 100% identical to SEQ ID NO:1, including all values and ranges there between. Fragments or segments of the polypeptide can include 5, 10, 20, 30, 40, 50, 60, 70, 80, 90, 100, 110, 120, 130, 140, 150, or 155 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155, and ending at amino acid 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160. Preferably, the segment is a functional segment maintaining cytoxicity against cancer cells. In still further aspects an ECP polypeptide can be modified by chemical modification of amino acid side chains (e.g., crosslinking, glycosylation, etc.) or by including heterologous peptide sequences at the amino or carboxy terminus of the peptide. In some embodiments, the ECP polypeptide is glycosylated.

In certain aspects neutrophil elastase (ELANE) or variant thereof has an amino acid sequence that is 90, 92, 94, 69, 98, 99, to 100% identical, including all values and ranges there between, 50, 75, 100, 125, 150, 175, 200, 225, 250, or 260 contiguous amino acids, including all values and there between to MTLGRRLACLF ranges LACVL-PALLLGGTALASEIVGGRRAR-PHAWPFMVSLQLRGGHFCGATLIAPNFVMS AAHC-VANVNVRAVRVVLGAHNLSRREPTRQVFAVQRIFEN GYDPVNLLNDIVILQL NGSATINANVQVAQL-PAQGRRLGNGVQCLAMGWGLL-GRNRGIASVLQELNVTVVT SLCRRSNVCTLVR-GRQAGVCFGDSGSPLVCNGLIHGIASFVRGGCASGLY PDAFAPV AQFVNWIDSIIQRSEDNPCPHPRDPDPAS-RTH (SEQ ID NO:2). Other aspects are directed to an ELANE polypeptide or variant thereof having 50, 75, 100, 125, 150, 175, 200, 225, 250, or 260 contiguous amino acids of the ELANE that is 90, 92, 94, 69, 98, 99, to 100% identical to SEQ ID NO:2, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, or 262, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, or 267. Preferably, the segment is a functional segment maintaining cytoxicity against cancer cells. Being that the inventors have determined that the catalytic activity is not required for ELANE cytotoxicity, the compositions and methods can also include modified ELANE that maintains cytoxicity against cancer cells, but does not retain the serine protease activity of ELANE. For example, an ELANE variant can have amino substitutions at one or more of amino acid H70, D117, and S202, which form the catalytic triad of this serine protease, as well as other mutations that inhibit enzyme activity. In still further aspects an ELANE polypeptide can be modified by chemical modification of amino acid side chains (e.g., crosslinking, glycosylation, etc.) or by including heterologous peptide sequences at the amino or carboxy terminus of the peptide. In certain aspect the ELANE polypeptide is glycosylated.

Certain embodiments are directed to a therapeutic or anti-cancer composition including various combinations of the two neutrophil secreted factors, or variants thereof. In certain aspects, a polypeptide composition can include (1) ELANE, or (2) ELANE and ECP. In certain aspects, the anti-cancer composition can include an effective amount of an ELANE polypeptide. In particular embodiments the composition includes ELANE and ECP. Polypeptides can be present in a composition at a ratio 0, 1, 2, 3, 4, or 5 ELANE to 0, 1, 2, 3, 4, or 5 ECP, wherein at least 1 or 2 polypeptides are present in the composition. The polypeptides can be present in a composition, or individually, at a concentration of 1, 50, 100, 150, 200, 250, 300, 350, 400, 450 µg/mL to 500, 550, 600, 650, 700, 750, 800, 850, 900, 950 µg/mL; or 1, 10, 20, 30, 40, 50, 60, 70, 80, 90 mg/mL to 100, 110, 120, 130, 140, 150, 160, 170, 180, 190, 200 mg/mL, including all ranges and values there between. In certain aspects, any one polypeptide of the composition can be, but not necessarily, associated or complexed with the other polypeptide. If associated or complexed, the polypeptides can be covalently or non-covalently associated. In other aspects, a therapeutic composition can include or be used in combination with one or more ELANE activator, for example, a comound or component that inhibits an ELANE inhibitor. Activators of ELANE include, but are not limited to alpha-1-anti-trypsin (A1AT), secretory leukocyte peptidase inhibitor (SLPI), serpin family B member 1 (SERPINB1), plasminogen activator inhibitor 1 (PAI1), antithrobmin (ATIII), and the like.

Compositions described herein can kill a wide variety of cancer cells, irrespective of cancer cell genetics. Thus, compositions described herein can treat various types of cancers. In certain aspects, the cancer is a bladder, blood, bone (e.g., osteosarcoma), bone marrow (e.g., leukemia), brain/nervous system (e.g., neuroblastoma, glioblastoma), breast, colorectal (e.g., colon carcinoma), esophageal, gastrointestinal, head, kidney, liver (e.g., hepatocellular carcinoma), lung (e.g., non-small cell lung cancer), nasopharynx, neck, ovarian, pancreatic, prostate, skin (e.g., melanoma), stomach, testicular, tongue, or uterine cancer. Compositions of described herein are toxic to cancer cells, but are not toxic or have a limited toxicity to non-cancer cells.

Certain embodiments are directed to methods for treating cancer comprising administering an effective amount of a therapeutic composition to a patient that has cancer. In certain aspects, the cancer is a bladder, blood, bone, bone marrow, brain, breast, colorectal, esophageal, gastrointestinal, head, kidney, liver, lung, nasopharynx, neck, ovarian, pancreatic, prostate, skin, stomach, testicular, tongue, or uterine cancer. In certain aspects, the polypeptide composition can further comprise additional anticancer agents to enhance the effectiveness of the polypeptide composition. In certain aspects, these additional anticancer agents can be administered before; during; after; before and during; before and after; during and after; or before, during and after administration of the polypeptide composition. In certain aspects, a composition described herein can be administered before; during; after; before and during; before and after; during and after; or before, during and after administration of an immunotherapy, a chemotherapy, a radio therapy, or a targeted therapy (e.g., anti-hormone therapy, etc.). Certain instance include methods for treating cancer that include the compositions described here administered in combination with signal transduction inhibitors, gene expression modulators, apoptosis inducers, angiogenesis inhibitors, anticancer antibodies (e.g., monoclonal antibodies) and the like. In certain aspects, a polypeptide composition of described herein is administered in combination with a chemotherapy, e.g., doxorubicin and/or paclitaxel.

In other aspects, the protein compositions can be used as an anti-bacterial. In certain aspects, a polypeptide composition as described herein can be used to mitigate or treat a *P. Aeruginosa, A. baumannii, P. aeruginosa*, or *K. pneumonia* infection.

One solution to abrogate the off-target toxicity of FASL related cancer therapy is the development of cancer therapies that target CD95 for degradation resulting in the killing of cancer cells while leaving healthy cells intact. One method of such a targeted therapy is the use of protease compositions that degrade CD95 and induce cancer cell specific apoptosis. The CD95 degrading protease compositions can be used in combination with radiotherapy, chemotherapy, immunotherapy, or anti-hormone therapy to improve the effectiveness of cancer killing. The inventors have discovered that certain proteases have the capacity to kill a broad range of cancer cells. In certain aspects, the protease(s) minimally affect the viability of non-cancer cells and can have minimal to no negative side effects.

Five CD95 degrading polypeptides have been identified by the inventors: (1) cathepsin G (CTSG), (2) proteinase 3 (PRTN3), (3) murine neutrophil elastase (mELANE), (4) porcine pancreatic elastase (PPE/pELA1), rat pancreatic elastase (RPE/rELA1) and (5) human neutrophil elastase (ELANE). The inventors have determined that these components and variants thereof have a cancer specific killing capability.

Cathepsin G (CTSG) is a member of the peptidase S1 protein family and is found in azurophil granules of neutrophilic polymorphonuclear leukocytes. This protease has a specificity similar to that of chymotrypsin C, and may participate in the killing and digestion of engulfed pathogens, and in connective tissue remodeling at sites of inflammation. GenPept accession number NP_001902.1 describes the cathepsin G preproprotein of *Homo sapiens*. The CTSG preprotein has an amino acid sequence of MQPLLLLLAFLLPTGAEAGEIIGGRESRPHSRPYMAYLQIQSPAGQSRCGGFL VREDF VLTAAHCWGSNINVTLGAHNIQRRENTQQHITARRAIRHPQYNQRTIQ NDIMLLQLS RRVRRNRNVNPVALPRAQEGLRPGTLCTVAGWGRVSMRRGTDTLREVQLR VQRDR QCLRIFGSYDPRRQICVGDRRERKAAFKGDSGGPLLCNNVAHGIVSYGKSSGVPPEV FTRVSSFLPWIRTTMRSFKLLDQMETPL (SEQ ID NO:3). In certain aspects a CTSG polypeptide or variant thereof has an amino acid sequence that is 90, 92, 94, 96, 98, 99, to 100% identical, including all values and ranges there between, over 50, 60, 70, 80, 90, 100, 110, 120, 130, 140, 150, 160, 170, 180, 190, 200, 210, 220, 230, 240, 250 or 255 contiguous amino acids, including all values and ranges there between, of SEQ ID NO:3. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, or 250 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, or 250 and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, or 255. In certain aspects, a CTSG polypeptide can be a functional polypeptide segment maintaining the capability to degrade CD95 and induce cancer cell death. In certain aspects, a polypeptide segment includes 50, 60, 70, 80, 90, 100, 110, 120, 130, 140, 150, 160, 170, 180, 190, 200, 210, 220, 230, 240, or 250 contiguous amino acids, including all values and ranges there between, of SEQ ID NO:3. In particular aspects a CTSG polypeptide can include amino acids 21 to 241 of SEQ ID NO:3 (trypsin-like protease domain). In still further aspects an CTSG polypeptide can be modified by chemical modification of amino acid side chains (e.g., crosslinking, glycosylation, etc.) or by including heterologous peptide sequences at the amino or carboxy terminus of the peptide.

Proteinase 3 (PRTN3) is a serine protease enzyme expressed mainly in neutrophil granulocytes. Its exact role in the function of the neutrophil is unknown, but, in human neutrophils, proteinase 3 contributes to the proteolytic generation of antimicrobial peptides. It is also the target of anti-neutrophil cytoplasmic antibodies (ANCAs) of the c-ANCA (cytoplasmic subtype) class, a type of antibody frequently found in the disease granulomatosis with polyangiitis (formerly known as "Wegener's granulomatosis"). GenPept accession number NP_002768.3 describes the PRTN3 of *Homo sapiens*. The PRNT3 protein has an amino acid sequence of MAHRPPSPALASVL-LALLLSGAARAAEIVGGHEAQPHSRPY-MASLQMRGNP GSHFCGGTLIHPSFVLTAAHCLR-DIPQRLVNVVLGAHNVRTQEPTQQHFSVAQVFLN NYDAENKLNDVLLIQLSSPANLSAS-VATVQLPQQDQPVPHGTQCLAMGWGRVGAH DPPAQVLQELNVTVVTFFCRPHNICTFVPRRKAG-ICFGDSGGPLICDGIIQGIDSFVIW GCATRLFPDFFTR-VALYVDWIRSTLRRVEAKGRP (SEQ ID NO:4). In certain aspects, a PRNT3 polypeptide or variant thereof has an amino acid sequence that is 90, 92, 94, 96, 98, 99, to 100% identical, including all values and ranges there between, over 50, 60, 70, 80, 90, 100, 110, 120, 130, 140, 150, 160, 170, 180, 190, 200, 210, 220, 230, 240, 250 or 256 contiguous amino acids, including all values and ranges there between, of SEQ ID NO:4. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, or 250 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, or 251, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, or 256. In certain aspects a PRTN3 polypeptide can be a functional polypeptide segment maintaining the capability to degrade CD95 and induce cancer cell death. In certain aspects, a polypeptide segment includes 50, 60, 70, 80, 90, 100, 110, 120, 130, 140, 150, 160, 170, 180, 190, 200, 210, 220, 230, 240, or 250 contiguous amino acids, including all values and ranges there between, of SEQ ID NO:4. In particular aspects a PRNT3 polypeptide can include amino acids 28 to 246 of SEQ ID NO:4 (trypsin-like protease domain). In still further aspects a PRNT3 polypeptide can be modified by chemical modification of amino acid side chains (e.g., crosslinking, glycosylation, etc.) or by including heterologous peptide sequences at the amino or carboxy terminus of the peptide.

In certain aspects, neutrophil elastase (ELANE) or variant thereof has an amino acid sequence that is 90, 92, 94, 69, 98, 99, to 100% identical, including all values and ranges there between, 50, 75, 100, 125, 150, 175, 200, 225, 250, or 260 contiguous amino acids, including all values and ranges there between to MTLGRRLACLFLACVLPALLLGGTA-LASE IVGGRRARPHAWPFMVSLQLRGGHFC-GATLIAPNFVMSAAHCVANVNVRAVRVVL GAHNLSRREPTRQVFAVQRIFENGYDPVNLLNDIV-ILQLNGSATINANVQVAQLPAQ GRRLGNGVQCLAMGWGLL-GRNRGIASVLQELNVTVVTSLCRRSNVCTLVR-GRQAG VCFGDSGSPLVCNGLIHGIASFVRGGCASG-LYPDAFAPVAQFVNWIDSIIQRSEDNPC PHPRDPDPASRTH (SEQ ID NO:2). Other aspects are directed to an ELANE polypeptide or variant thereof having 50, 75, 100, 125, 150, 175, 200, 225, 250, or 260 contiguous amino acids of the ELANE that is 90, 92, 94, 69, 98, 99, to 100% identical to SEQ ID NO:2, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, or 262, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, or 267. Certain aspects are directed to a ELANE a functional polypeptide segment that maintains cytoxicity against cancer cells. In certain aspects, a polypeptide segment includes 50, 60, 70, 80, 90, 100, 110, 120, 130, 140, 150, 160, 170, 180, 190, 200, 210, 220, 230, 240, or 250 contiguous amino acids, including all values and ranges there between, of SEQ ID NO:2. In still further aspects an ELANE polypeptide can be modified by chemical modification of amino acid side chains (e.g., crosslinking, glycosylation, etc.) or by including heterologous peptide sequences at the amino or carboxy terminus of the peptide. In certain aspect the ELANE polypeptide is glycosylated.

In certain aspects, a murine neutrophil elastase (mELANE) or variant thereof can be used, which has an amino acid sequence that is 90, 92, 94, 69, 98, 99, to 100% identical, including all values and ranges there between, 50, 75, 100, 125, 150, 175, 200, 225, 250, or 260 contiguous amino acids, including all values and ranges there between to MALGRLSSRTLAAMLLALFLGGPALASEIVGGR-PARPHAWPFMASLQRRGGHFCGA TLIARNFVM-SAAHCVNGLNFRSVQVVLGAHDLRRQER-TRQTFSVQRIFENGFDPSQL LNDIVIIQLNGSATINANVQVAQL-PAQGQGVGDRTPCLAMGWGRLGTNRPSPSVLQE LNVTVVTNMCRRRVNVCTLVPRRQAGICFGDSGG-PLVCNNLVQGIDSFIRGGCGSGL YPDAFAPVAEFAD-WINSIIRSHNDHLLTHPKDREGRTN (SEQ ID NO:5) (GenPept accession number NP_056594.2). Other aspects are directed to an mELANE polypeptide or variant thereof having 50, 75, 100, 125, 150, 175, 200, 225, 250, or 265 contiguous amino acids of the mELANE that is 90, 92, 94, 69, 98, 99, to 100% identical to SEQ ID NO:5, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, or 260, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265. In certain aspects, a mELANE polypeptide can be a functional polypeptide segment maintaining the capability to degrade CD95 and induce cancer cell death. In certain aspects, a polypeptide segment includes 50, 60, 70, 80, 90, 100, 110, 120, 130, 140, 150, 160, 170, 180, 190, 200, 210, 220, 230, 240, or 250 contiguous amino acids, including all values and ranges there between, of SEQ ID NO:5. In particular aspects a mELANE polypeptide can include amino acids 29 to 245 of SEQ ID NO:5 (trypsin-like protease domain).

In certain aspects, a porcine pancreatic elastase (pELA1) or variant thereof can be used, which has an amino acid sequence that is 90, 92, 94, 69, 98, 99, to 100% identical, including all values and ranges there between, 50, 75, 100, 125, 150, 175, 200, 225, 250, 260, to 266 contiguous amino acids, including all values and ranges there between of MLRLLVVASLVLYGHSTQDFPETNARVVGGTEA-QRNSWPSQISLQYRSGSSWAHTC GGT-LIRQNWVMTAAHCV-DRELTFRVVVGEHNLNQNDGTEQYVGVQKIVVHPY WN TDDVAAGYDIALLRLAQSVTLNSYVQLGVL-PRAGTILANNSPCYITGWGLTRINGQL AQTLQQAY-LPTVDYAICSSSSYWG-STVKNSMVCAGGDGVRSGCQGDSGGPLHCLV NGQYAVHGVTSFVSRLGCNVTRKPTVFTRVSAY-ISWINNVIASN (SEQ ID NO:6) (SP accession number P00772). Other aspects are directed to an pELA1 polypeptide or variant thereof having 50, 75, 100, 125, 150, 175, 200, 225, 250, or 265 contiguous amino acids of the pELA1 that is 90, 92, 94, 69, 98, 99, to 100% identical to SEQ ID NO:6, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, or 261, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, or 266. In certain aspects, a pELA1 polypeptide is a functional polypeptide segment maintaining the capability to degrade CD95 and induce cancer cell death. In certain aspects, a polypeptide segment includes 50, 60, 70, 80, 90, 100, 110, 120, 130, 140, 150, 160, 170, 180, 190, 200, 210, 220, 230, 240, 250 or 265 contiguous amino acids, including all values and ranges there between, of SEQ ID NO:6. In particular aspects a pELA1 polypeptide can include amino acids 60 to 275 of SEQ ID NO:6 (trypsin-like protease domain).

Certain embodiments are directed to a therapeutic or anti-cancer composition including various combinations of CD95 degrading proteases or variants thereof, or expression vector or expression cassette encoding the same. In certain aspects, a polypeptide composition can include one or more of (1) cathepsin G (CTSG), (2) proteinase 3 (PRTN3), (3) murine neutrophil elastase (mELANE), (4) porcine pancreatic elastase (pELA1), or (5) human neutrophil elastase (ELANE). The polypeptides can be present in a composition, individually, at a concentration of 1, 50, 100, 150, 200, 250, 300, 350, 400, 450 µg/mL to 500, 550, 600, 650, 700, 750, 800, 850, 900, 950 µg/mL; or 1, 10, 20, 30, 40, 50, 60, 70, 80, 90 mg/mL to 100, 110, 120, 130, 140, 150, 160, 170, 180, 190, 200 mg/mL, including all ranges and values there between.

Compositions described herein can kill a wide variety of cancer cells, irrespective of cancer cell genetics. Thus, compositions described herein can treat various types of cancers. In certain aspects, the cancer is a bladder, blood, bone (e.g., osteosarcoma), bone marrow (e.g., leukemia), brain/nervous system (e.g., neuroblastoma, glioblastoma), breast, colorectal (e.g., colon carcinoma), esophageal, gastrointestinal, head, kidney, liver (e.g., hepatocellular carcinoma), lung (e.g., non-small cell lung cancer), nasopharynx, neck, ovarian, pancreatic, prostate, skin (e.g., melanoma), stomach, testicular, tongue, or uterine cancer. Compositions described herein are toxic to cancer cells, but are not toxic or have a limited toxicity to non-cancer cells.

Certain embodiments are directed to methods for killing a cancer cell by CD95 degradation comprising administering an effective amount of a therapeutic composition to a patient that has cancer. In certain aspects, the cancer is a bladder, blood, bone, bone marrow, brain, breast, colorectal, esophageal, gastrointestinal, head, kidney, liver, lung, nasopharynx, neck, ovarian, pancreatic, prostate, skin, stomach, testicular, tongue, or uterine cancer. In certain aspects the polypeptide composition can further comprise additional anticancer agents to enhance the effectiveness of the polypeptide composition. In certain aspects, these additional anticancer agents can be administered before; during; after; before and during; before and after; during and after; or before, during and after administration of the polypeptide composition. In certain aspects, a composition described herein can be administered before; during; after; before and during; before and after; during and after; or before, during and after administration of an immunotherapy, a chemotherapy, an anti-hormone therapy, or a radiotherapy. In certain aspects a polypeptide composition of described herein is administered in combination with a chemotherapy, e.g., doxorubicin and/or paclitaxel.

Certain embodiments are directed to an expression vector or expression cassette encoding all or a segment of a protease, serine protease, or neutrophil derived serine protease, in particular those polypeptides described herein. A subject can be administered such a vector or cassette for the purpose of expressing a protease in or in proximity to a target cell to affect degradation of CD95 in a target cell.

The term "effective amount" means an amount effective, at dosages and for periods of time necessary, to achieve the desired therapeutic or prophylactic result.

An "effective amount" of an anti-cancer agent (e.g., polypeptide composition described herein) in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e., reduce tumor burden); lessen or reduce the number of cancerous cells in the body; prevent recurrence of cancer after surgical removal or other anti-cancer therapies; or ameliorate or alleviate the symptoms of the disease caused by the cancer.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

A variety of embodiments are discussed throughout this application. Any embodiment discussed with respect to one aspect applies to other aspects as well and vice versa. Each embodiment described herein is understood to be embodiments that are applicable to all aspects. It is contemplated that any embodiment discussed herein can be implemented with respect to any method or composition, and vice versa. Furthermore, compositions and kits can be used to achieve methods disclosed herein.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that embodiments described herein in the context of the term "comprising" may also be implemented in the context of the term "consisting of" or "consisting essentially of."

Other embodiments are discussed throughout this application. Any embodiment discussed with respect to one aspect applies to other aspects as well and vice versa. The embodiments in the Example section are understood to be embodiments that are applicable to all aspects.

Other objects, features and advantages of the present invention will become apparent from the following detailed description. It should be understood, however, that the detailed description and the specific examples, while indicating specific embodiments, are given by way of illustration only, since various changes and modifications within the spirit and scope will become apparent to those skilled in the art from this detailed description.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Any embodiment disclosed herein can be implemented or combined with any other embodiment disclosed herein, including aspects of embodiments for compounds can be combined and/or substituted and any and all compounds can be implemented in the context of any method described herein. Similarly, aspects of any method embodiment can be combined and/or substituted with any other method embodiment disclosed herein. Moreover, any method disclosed herein may be recited in the form of "use of a composition" for achieving the method. It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Figure 19:
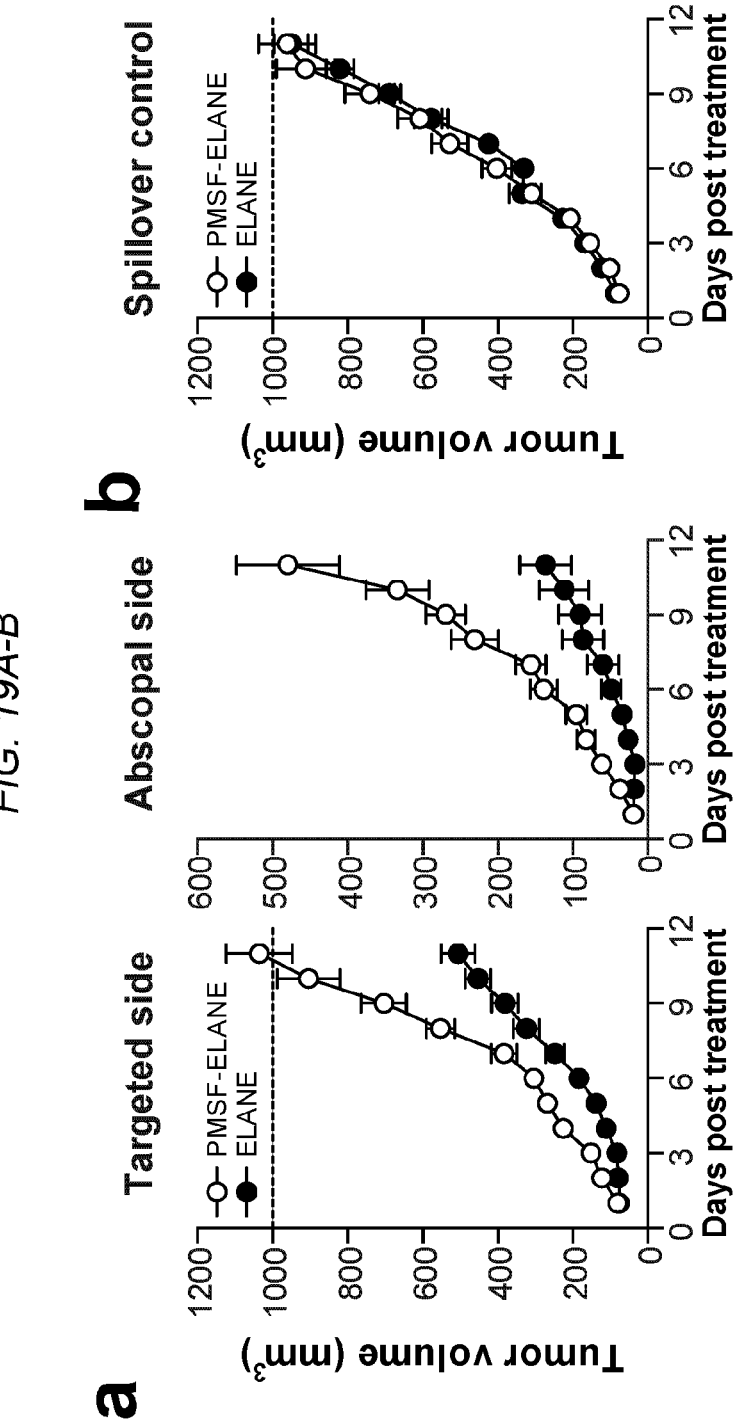

FIG. 19A-B. Intra-tumorally delivered ELANE induces an abscopal effect. (a) E0771 cancer cells were injected into left (0.5 million cells) and right (0.4 million cells) mammary fat pad of C57BL/6 mice. Once tumors on the left side reached ~100 mm³, ELANE (11.6 μg) or PMSF-inactivated ELANE (PMSF-ELANE) were injected intra-tumorally into the left tumor once/day for 5 days. n=10 mice/group. No action was performed on the right side of the tumor (abscopal side). Tumor volume on both sides were measured by calipers. (B) To eliminate the possibility that the abscopal effect was due to spillover of ELANE from the left to the right tumor, E0771 cancer cells were injected only into the left mammary fat pad of C57BL/6 mice, and mice were treated daily with ELANE (11.6 μg) or PMSF-ELANE into the right mammary fat pad. Tumor volume was measured by calipers. Results show that ELANE does not lower tumor growth when it is injected to the contralateral (non-tumor bearing) mammary fat pad.

Figure 20:
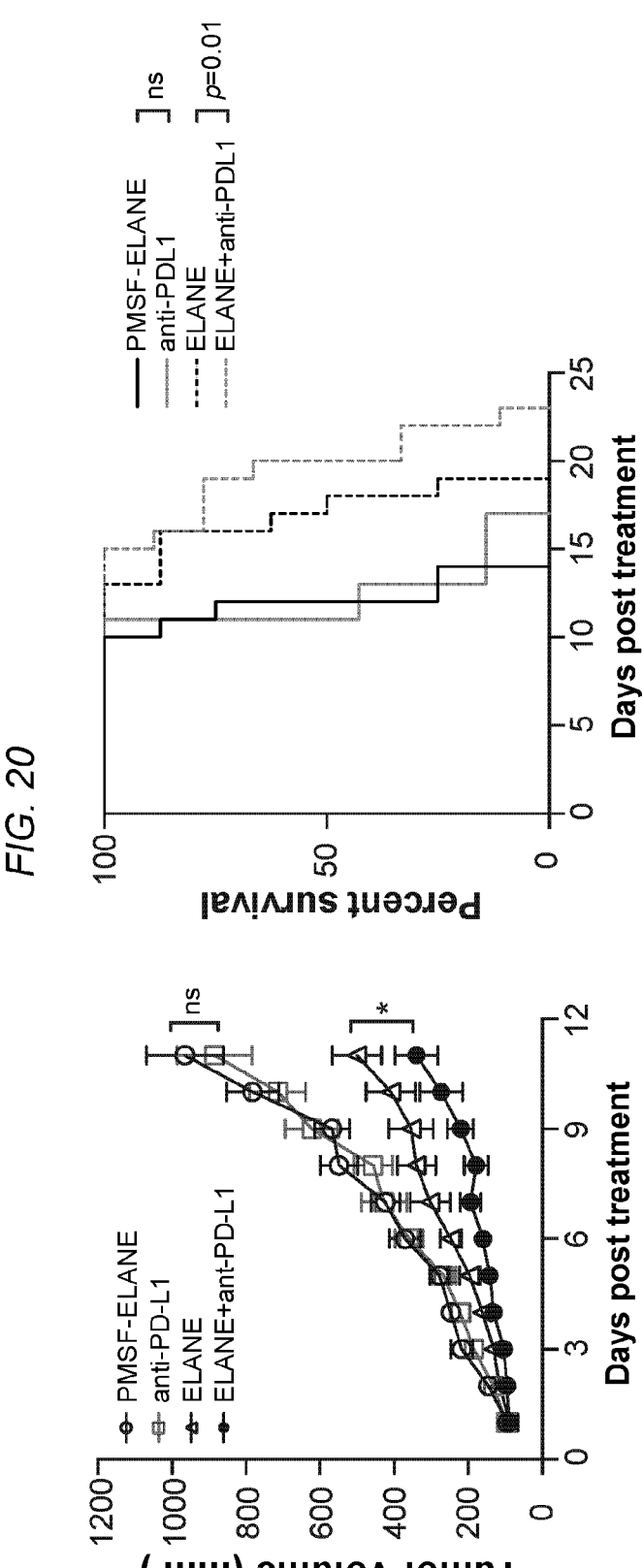

FIG. 20. Intra-tumorally delivered ELANE enables anti-PDL1 efficacy in a mouse model of TNBC. E0771 cancer cells were injected into C57BL/6 mice. Once tumors reached ~100 mm³, mice were randomly separated into four groups: ELANE (11.6 μg), PMSF-inactivated ELANE (PMSF-ELANE), anti-PD-L1 (BioXCell, 10F.9G2, 100 μg), and ELANE (11.6 μg)+anti-PD-L1 (100 μg). n=8-9 mice/group. Anti-PD-L1 monoclonal antibody was injected intaperitoneally on days 10, 14, 18, and 22 after tumor inoculation. ELANE or PMSF-ELANE were delivered intra-tumorally when tumors reached ~80 mm³ (~14 days post cancer cell injection). Tumor volume was measured by calipers. Kaplan-Meier curve was plotted and the logrank test (Mentel-Cox method) was used for mouse survival analysis. End point of survival is defined as tumor volume >1000 mm³. *, p<0.05, Student's t-test.

FIG. 21A-D. ELANE does not produce evident toxicity. Human serum albumin (HSA; 11.6 μg)) or ELANE (11.6 μg) was injected into the mammary fat pad of healthy non-tumor-bearing C57BL/6 mice once a day for 5 consecutive days, and side effects were monitored. (a) Immunohistochemistry staining for apoptosis markers (TUNEL, cleaved CASP3 (c-CASP3), cleaved PARP (c-PARP)) 2 days after the final injection. (b) Delta body weight. (c) Spleen weight. (c) Blood ALT activity levels (a marker of liver function).

DESCRIPTION

Neutrophils are the most abundant immune cell population with 50-70% of all leukocytes. About $10^{11}$ neutrophils/day are produced with an increase in production in subjects with cancer. Neutrophils in tumor-bearing hosts can oppose or potentiate tumor progression. Tumors are known to release molecules that promote neutrophil release from bone marrow, which can result in premature neutrophils being released. These neutrophils may differentiate at inflammatory sites or a tumor primes immature neutrophils for functions they would not ordinarily perform. Normally neutrophils have half-lives of 7 hours in humans, but in tumors the tumor associated cytokines prolong their half-lives to 17 hours. Neutrophil polarization leads to divergent phenotypes, depending on specific tumor derived factors. Some factors activate a tumor and metastasis-promoting program, while others act as a negative regulator of the pro-tumorigenic phenotype of neutrophils. Cytokine concentration and tumor physiology (such as hypoxia) may play a role in neutrophil polarization because cytotoxic neutrophils are turned in to tumor promoting cells as tumors expand and evolve.

Neutrophil derived elastase and the immunosuppressive ability of neutrophils has been implicated in tumor initiation. There is uncertainty if neutrophils are cancer promoting or anti-tumorigenic. The literature tends to point towards the tumor-promoting role of neutrophils. Several mitogenic and pro-angiogenic molecules have been implicated in neutrophil-driven tumor growth including elastase, prokineticin 2 (PROK2, also known as BV8) and MMP9.

Neutrophils are potent effectors of angiogenesis and can also attract cancer cells towards endothelial cells to promote intravasation into the circulation. An interesting consequence of tumor expansion at the primary site is the accumulation of neutrophils in visceral organs before the arrival of disseminated cancer cells.

In other aspects, the inventors have identified CD95 degradation as the mechanism of action by which ELANE kills cancer cells, and further show that a broad range of proteases can mimic ELANE's CD95 degradation and cancer cell killing properties. Aspects of the invention are based partially on the following observations. Treating ELANE or neutrophil conditioned media with alpha-1-antitrypsin or PMSF, two irreversible non-competitive ELANE inhibitors, protects cancer cells from apoptosis. Incubating ELANE with ECP increases its enzyme activity. The inventors have shown that ECP acts as a type 2 allosteric activator of ELANE that increases kcat for its substrate by 12-fold without altering KM. These studies also determined that ECP binds ELANE with very strong affinity ($K_D$~20 nM). ELANE degrades the C-terminal domain of purified CD95. Importantly, this cleavage pattern was distinct from that produced by MMP7, which was previously shown to cleave the extracellular N-terminal domain of CD95, resulting in protection of cancer cells from FASL-mediated apoptosis (Strand et al., *Oncogene*, 2004). Incubating cancer cells with ELANE results in CD95 loss from the cell surface. Flow cytometry experiments showed that CD95-low cancer cells stained positive for two markers of cell death including high annexin V and propidium iodide staining. Other serine proteases including CTSG, PRTN3, and ELANE from other species (murine neutrophil elastase or porcine pancreatic elastase) cleaved purified CD95 with an identical degradation pattern to ELANE, and these proteases also killed cancer cells.

The efficiency by which these proteases cleaved CD95 was well correlated with their ability to kill cancer cells. Thus, targeting CD95 for degradation offers three important advantages over the FASL and siRNA/shRNA approaches described above. First, unlike the resistance reported with FASL, the inventors have shown that cancer cells are incapable of becoming resistant to this degradative pathway in vitro and in vivo. Second, the inventors have shown that intratumoral delivery of purified ELANE (or ELANE and ECP) in multiple mouse cancer models induced widespread apoptosis using a CD95 degradation pathway. These findings suggest that the therapeutic proteins do not suffer from the delivery and instability problems reported for the siRNA/shRNA approach. Third, the inventors have shown that the therapeutic proteins are not toxic to non-cancer cells, including T-cells. Treating human blood Tcells with these ELANE (or ELANE and ECP) did not induce apoptosis in vitro. Moreover, injecting these proteins into mice with or without cancer did not deplete T-cells. Thus, unlike the siRNA/shRNA approach, the therapeutic proteins described herein do not deplete T-cells or suppress anti-tumor immunity. In fact, when tumor bearing mice were treated with ELANE, tumor and splenic T-cells numbers were elevated. These increases were specific to tumor bearing mice, since injecting ELANE into non-tumor bearing mice did not produce similar effects. These findings suggest that the cancer cell apoptosis induced by ELANE, triggered a strong anti-tumor adaptive immune response. Fourth, unlike the FASL approach, therapeutic compositions do not induce liver toxicity in vivo.

I. Compositions

A. Neutrophil Secreted Factors

The inventors have discovered neutrophil secreted factors that have the capacity to kill a broad range of cancer cells without significantly affecting the viability of non-cancer cells. Two neutrophil killing factors have been identified by the inventors: (1) eosinophil cationic protein (ECP), and (2) neutrophil elastase (ELANE). The inventors have further evidence that these components complement or synergize with one another. In particular embodiments ELANE and/or ECP are effective alone, or in combination with each other. Certain embodiments are directed to composition comprising one or both polypeptides, including variants, described herein.

These factors were identified by (a) obtaining blood from healthy donors, (b) developing a method for isolating peripheral blood neutrophils and obtaining neutrophil secreted factors, (c) developing a method for quantifying cancer cell death in a 96-well plate format, (d) developing a method for fractionating neutrophil conditioned media using filters and columns, (e) developing a method for proteomics analysis of neutrophil conditioned media and fractions from columns, (f) developing a method for depleting the neutrophil conditioned media of specific proteins of interest and testing effect on cancer cell killing, (g) confirming observations using purified recombinant proteins, (h) optimizing combinations of proteins for anti-cancer effects.

1. Eosinophil Cationic Protein (ECP)

Eosinophil Cationic Protein (ECP), also known as ribonuclease 3, is a basic protein located in the eosinophil primary matrix (protein accession number NP_002926, SEQ ID NO: 1). The ECP protein is released during degranulation of eosinophils. There are three glycosolated forms of ECP and consequently ECP has a range of molecular weights from 18-22 kDa. ECP can be used to increase the acitivity of serine protease and can be used in combination with a variety of serine proteases.

ECP has a number of biological activities, including suppression of T-cell proliferative responses and immunoglobulin synthesis by B cells, mast cell degranulation, regulation of fibroblast activities, induction of airway mucus secretion, and interaction with the coagulation and complement systems. ECP also demonstrates cytotoxic activity against bacteria, parasites, viruses, respiratory epithelial, and cancer cells. The mechanism of action of ECP is mediated through its cytotoxic capacity to create pores in the cell membrane, with ensuing destabilization of the phospholipid bilayer and osmotic cell lysis.

2. Neutrophil Elastase (ELANE)

Neutrophil elastase is a serine proteinase in the same family as chymotrypsin and has broad substrate specificity (protein accession number NP_001963, SEQ ID NO:2). The protein is secreted by neutrophils and macrophages during inflammation, it destroys bacteria and host tissue. It also localizes to Neutrophil extracellular traps (NETs), via its high affinity for DNA, an unusual property for serine proteases. As with other serine proteinases it contains a charge relay system composed of the catalytic triad of histidine, aspartate, and serine residues that are dispersed throughout the primary sequence of the polypeptide, which are brought together in the three-dimensional conformation of the folded protein. Neutrophil elastase is closely related to other cytotoxic immune serine proteases, such as the granzymes and cathepsin G. The neutrophil form of elastase is 218 amino acids long, with two asparagine-linked carbohydrate chains. It is present in azurophil granules in the neutrophil cytoplasm.

ELANE has broad substrate specificity under physiological conditions, and excessive ELANE results in digestion of not only elastin, but also other extracellular matrix proteins. The amount of immunoreactive NE in tumor tissue is an independent prognostic indicator of patients with breast cancer and lung cancer. Specific ELANE inhibitors (e.g., sivelestat and elafin) have been shown to suppress growth of cancer cells transplanted into severe combined immunodeficiency mice, implicating ELANE released from activated neutrophils stimulates the growth and progression of cancer cells, suggesting that ELANE catalytic activity is required for its pro-tumorigenic function. In contrast, the inventors have found that ELANE possesses strong cancer cell killing capability.

B. Protease Compositions

The inventors have discovered various proteases that have the capacity to kill a broad range of cancer cells without significantly affecting the viability of non-cancer cells. Such proteases include: (1) cathepsin G (CTSG), (2) proteinase 3 (PRTN3), (3) murine neutrophil elastase (mELANE), (4) murine pancreatic elastase (mELA1) (5) porcine pancreatic elastase (pELA1), (6) rat pancreatic elastase (rELA1/RPE) and (7) human neutrophil elastase (ELANE).

1. Cathepsin G (CTSG)

Cathepsin G (CTSG) is a member of the peptidase S1 protein family and is found in azurophil granules of neutrophilic polymorphonuclear leukocytes. This protease has a specificity similar to that of chymotrypsin C, and may participate in the killing and digestion of engulfed pathogens, and in connective tissue remodeling at sites of inflammation. GenPept accession number NP_001902.1 describes the cathepsin G preproprotein of *Homo sapiens*. (SEQ ID NO:3). In certain aspects a CTSG polypeptide or variant thereof has an amino acid sequence that is 90, 92, 94, 96, 98, 99, to 100% identical, including all values and ranges there between, over 50, 60, 70, 80, 90, 100, 110, 120, 130, 140, 150, 160, 170, 180, 190, 200, 210, 220, 230, 240, 250 or 255 contiguous amino acids, including all values and ranges there between, of SEQ ID NO:3. The segment is a functional segment maintaining the capability to degrade CD95 and/or induce cancer cell death. In particular aspects a CTSG polypeptide can include amino acids 21 to 241 of SEQ ID NO:3 (trypsin-like protease domain). In still further aspects an CTSG polypeptide can be modified by chemical modification of amino acid side chains (e.g., crosslinking, glycosylation, etc.) or by including heterologous peptide sequences at the amino or carboxy terminus of the peptide.

2. Proteinase 3 (PRTN3)

Proteinase 3 (PRTN3) is a serine protease enzyme expressed mainly in neutrophil granulocytes. Its exact role in the function of the neutrophil is unknown, but, in human neutrophils, proteinase 3 contributes to the proteolytic generation of antimicrobial peptides. It is also the target of anti-neutrophil cytoplasmic antibodies (ANCAs) of the c-ANCA (cytoplasmic subtype) class, a type of antibody frequently found in the disease granulomatosis with poly-angiitis (formerly known as "Wegener's granulomatosis"). GenPept accession number NP 002768.3 describes the PRTN3 of *Homo sapiens* (SEQ ID NO:4). In certain aspects a PRNT3 polypeptide or variant thereof has an amino acid sequence that is 90, 92, 94, 96, 98, 99, to 100% identical, including all values and ranges there between, over 50, 60, 70, 80, 90, 100, 110, 120, 130, 140, 150, 160, 170, 180, 190, 200, 210, 220, 230, 240, 250 or 256 contiguous amino acids, including all values and ranges there between, of SEQ ID NO:4. The segment is a functional segment maintaining the capability to degrade CD95 and/or induce cancer cell death. In particular aspects a PRNT3 polypeptide can include amino acids 28 to 246 of SEQ ID NO:4 (trypsin-like protease domain). In still further aspects a PRNT3 polypep-tide can be modified by chemical modification of amino acid side chains (e.g., crosslinking, glycosylation, etc.) or by including heterologous peptide sequences at the amino or carboxy terminus of the peptide.

3. Neutrophil Elastase (ELANE)

Neutrophil elastase (ELANE) is a serine proteinase in the same family as chymotrypsin and has broad substrate speci-ficity (protein accession number NP_001963, SEQ ID NO:2). The protein is secreted by neutrophils and macrophages during inflammation, it destroys bacteria and host tissue. It also localizes to Neutrophil extracellular traps (NETs), via its high affinity for DNA, an unusual property for serine proteases. As with other serine proteinases it contains a charge relay system composed of the catalytic triad of histidine, aspartate, and serine residues that are dispersed throughout the primary sequence of the polypeptide, which are brought together in the three-dimensional conformation of the folded protein. Neutrophil elastase is closely related to other cytotoxic immune serine proteases, such as the granzymes and cathepsin G. The neutrophil form of elastase is 218 amino acids long, with two asparagine-linked carbo-hydrate chains. It is present in azurophil granules in the neutrophil cytoplasm.

ELANE has broad substrate specificity under physiologi-cal conditions, and excessive ELANE results in digestion of not only elastin, but also other extracellular matrix proteins. The amount of immunoreactive ELANE in tumor tissue is an independent prognostic indicator of patients with breast cancer and lung cancer. Specific ELANE inhibitors (e.g., sivelestat and elafin) have been shown to suppress growth of cancer cells transplanted into severe combined immunode-ficiency mice, suggesting that neutrophil-derived ELANE promotes tumorigenesis. However, we showed that while murine neutrophils (isolated from bone marrow, peritoneal cavity, or lung) release ELANE, this ELANE is catalytically inactive. Moreover, conditioned media collected from these murine neutrophils was incapable of killing cancer cells in vitro. Thus, the anti-cancer function of sivelestat and elafin observed in mice, is unlikely to mediated by their ability to inhibit neutrophil-derived ELANE catalytic activity.

In certain aspects, a human neutrophil elastase (ELANE) or variant thereof has an amino acid sequence that is 90, 92, 94, 69, 98, 99, to 100% identical, including all values and ranges there between, 50, 75, 100, 125, 150, 175, 200, 225, 250, or 260 contiguous amino acids, including all values and ranges there between to SEQ ID NO:2. Other aspects are directed to an ELANE polypeptide or variant thereof having 50, 75, 100, 125, 150, 175, 200, 225, 250, or 260 contiguous amino acids of the ELANE that is 90, 92, 94, 69, 98, 99, to 100% identical to SEQ ID NO:2, including all values and ranges there between. Preferably, the segment is a functional segment maintaining cytoxicity against cancer cells. In still further aspects an ELANE polypeptide can be modified by chemical modification of amino acid side chains (e.g., crosslinking, glycosylation, etc.) or by including heterolo-gous peptide sequences at the amino or carboxy terminus of the peptide. In certain aspects, the ELANE polypeptide is glycosylated.

In certain aspects, a murine neutrophil elastase (mELANE) or variant thereof can be used, which has an amino acid sequence that is 90, 92, 94, 69, 98, 99, to 100% identical, including all values and ranges there between, 50, 75, 100, 125, 150, 175, 200, 225, 250, or 260 contiguous amino acids, including all values and ranges there between to SEQ ID NO:5 (GenPept accession number NP_056594.2). Other aspects are directed to an mELANE polypeptide or variant thereof having 50, 75, 100, 125, 150, 175, 200, 225, 250, or 265 contiguous amino acids of the mELANE that is 90, 92, 94, 69, 98, 99, to 100% identical to SEQ ID NO:5, including all values and ranges there between. The segment is a functional segment maintaining the capability to degrade CD95 and induce cancer cell death. In particular aspects a mELANE polypeptide can include amino acids 29 to 245 of SEQ ID NO:5 (trypsin-like protease domain).

In certain aspects, a porcine pancreatic elastase (pELA1) or variant thereof can be used, which has an amino acid sequence that is 90, 92, 94, 69, 98, 99, to 100% identical, including all values and ranges there between, 50, 75, 100, 125, 150, 175, 200, 225, 250, 260, 270, 280, 290, to 297 contiguous amino acids, including all values and ranges there between, to SEQ ID NO:6 (GenBank accession num-ber xp_005655631 OR SP P0072). Other aspects are directed to an pELA1 polypeptide or variant thereof having 50, 75, 100, 125, 150, 175, 200, 225, 250, or 265 contiguous amino acids of the pELA1 that is 90, 92, 94, 69, 98, 99, to 100% identical to SEQ ID NO:6, including all values and ranges there between. The segment is a functional segment maintaining the capability to degrade CD95 and induce cancer cell death. In particular aspects a pELA1 polypeptide can include amino acids 67 to 302 of SEQ ID NO:6 (trypsin-like protease domain).

In certain aspects, a murine pancreatic elastase (mELA1) or variant thereof can be used, which has an amino acid sequence that is 90, 92, 94, 69, 98, 99, to 100% identical, including all values and ranges there between, 50, 75, 100, 125, 150, 175, 200, 225, 250, 260, 270, 280, 290, to 297 contiguous amino acids, including all values and ranges there between, to MLRFLVFASLVLCGHSTEDVPET-DARVVGGAEARRNSWPSQISLQYQYGGSWHHTC GGTLIRSNWVMTAAHCVDSPM-TYRVVVGEHNLSQNDGTEQYVNVQKIVSHPYWN KNNVVAGYDIALLRLAKSVTLNNYVQLGVLPREGTI-LANNSPCYITGWGRTRTNGEL AQTLQQAYLPSVSYS-ICSSSSYWGSSVKNTMVCAGGDGVRSGCQGDSGG-PLHCMV NGQYAVHGVTSFVSSMGCNVARKPTVFTRVSAY-ISWMNNVIASN SEQ ID NO:7 (GenPept accession num-ber NP_291090.2). Other aspects are directed to an mELA1 polypeptide or variant thereof having 50, 75, 100, 125, 150, 175, 200, 225, 250, or 265 contiguous amino acids of the mELA1 that is 90, 92, 94, 69, 98, 99, to 100% identical to SEQ ID NO: 7, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, or 261, and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, or 266. The segment is a functional segment maintaining the capability to degrade CD95 and induce cancer cell death. In particular aspects a mELA1 polypeptide can include amino acids 26 to 258 of SEQ ID NO: 7 (trypsin-like protease domain).

In certain aspects, a rat pancreatic elastase (rELA1/RPE) or variant thereof can be used, which has an amino acid sequence that is 90, 92, 94, 69, 98, 99, to 100% identical, including all values and ranges there between, 50, 75, 100, 125, 150, 175, 200, 225, 250, 260, to 266 contiguous amino acids, including all values and ranges there between, to MLRFLVFASLVLYGHSTQDFPETNARVVGGAEARRN-SWPSQISLQYLSGGSWYHTC GGT-LIRRNWVMTAAHCVSSQMTFRVVVGDHNLSQNDGT EQYVSVQKIVVHPNWNS NNVAAGYDIALLR-LAQSVTLNNYVQLAVLPQEGTI-LANNNPCYITGWGRTRINGQL SQTLQQAYLPSVDYS-ICSSSSYWGSTVKTTMVCAGGDGVRSGCQGDSGGPL HCLVN GQYSVHGVTSFVSSMGCNVSRKPTVFTRVSAY-ISWMNNVIAYN SEQ ID NO:8 (GenPept accession number NP_036684.1). Other aspects are directed to an rELA1 polypeptide or variant thereof having 50, 75, 100, 125, 150, 175, 200, 225, 250, or 265 contiguous amino acids of the rELA1 that is 90, 92, 94, 69, 98, 99, to 100% identical to SEQ ID NO: 8, including all values and ranges there between. Fragments or segments of the polypeptide can include 5, 10, 20, 30, 40, 50, 60, 70, 80, 90, 100, 110, 120, 130, 140, 150, 160, 170, 180, 190, 200, 210, 220, 230, 240, 250, or 260 contiguous amino acids (including all values and ranges there between) starting from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, or 264 and ending at amino acid 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, or 269. The segment is a functional segment maintaining the capability to degrade CD95 and induce cancer cell death. In particular aspects a rELA1 polypeptide can include amino acids 26 to 258 of SEQ ID NO: (trypsin-like protease domain).

C. Polypeptide Composition and Formulations

"Polypeptide" refers to any peptide or protein comprising amino acids joined by peptide bonds or modified peptide bonds. "Polypeptide" refers to short chains, including peptides, oligopeptides or oligomers, and to longer chains, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Modifications can occur anywhere in a polypeptide, including the peptide backbone, the amino acid side-chains, and the amino terminus or the carboxy terminus. It will be appreciated that the same type of modification may be present in the same or varying degrees at several sites in a given polypeptide. Also, a given polypeptide may contain many types of modifications. Modifications include terminal fusion (N- and/or C-terminal), acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

There are a wide variety of detectable labels that can be attached to polypeptides and variants thereof. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, OR, USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, OR, USA), and Cy2, Cy3, Cy3.5, Cy5, Cy5.5, Cy7. For secondary detection using labeled avidin, streptavidin, captavidin or neutravidin, the polypeptides can usefully be labeled with biotin. Polypeptides can be labeled with radioisotopes, such as $^{33}P$, $^{32}P$, $^{35}S$, $^{3}H$, and $^{125}I$. As another example, when the polypeptide may be used for targeted radiotherapy, the label can be $^{3}H$, $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99}mTc$, $^{97}Ru$, $^{90}Y$, $^{90}Sr$, $^{88}Y$, $^{72}Se$, $^{67}Cu$, or $^{47}Sc$.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

The term "amino acid" or "residue" should be understood to mean a compound containing an amino group ($NH_2$), a carboxylic acid group (COOH), and any of various side groups, that have the basic formula $NH_2CHRCOOH$, and that link together by peptide bonds to form proteins. Amino acids may, for example, be acidic, basic, aromatic, polar or derivatized. Non-standard amino acids may be referred to as "non-canonical" amino acids. Amino acids are naturally found in the $\alpha$- and L-form, however, $\beta$- and D-form amino acids can also be prepared.

A one-letter abbreviation system is frequently applied to designate the identities of the twenty "canonical" amino acid residues generally incorporated into naturally occurring peptides and proteins, these designation are well known in the art. Such one-letter abbreviations are entirely interchangeable in meaning with three-letter abbreviations, or non-abbreviated amino acid names. The canonical amino acids and their three letter and one letter codes include Alanine (Ala) A, Glutamine (Gln) Q, Leucine (Leu) L, Serine (Ser) S, Arginine (Arg)R, Glutamic Acid (Glu) E, Lysine (Lys) K, Threonine (Thr) T, Asparagine (Asn) N, Glycine (Gly) G, Methionine (Met) M, Tryptophan (Trp) W, Aspartic Acid (Asp) D, Histidine (His) H, Phenylalanine (Phe) F, Tyrosine (Tyr) Y, Cysteine (Cys) C, Isoleucine (Ile) I, Proline (Pro) P, and Valine (Val) V.

Certain embodiments also include variants of the polypeptides described herein. Variants of the disclosed polypeptides may be generated by making amino acid additions or insertions, amino acid deletions, amino acid substitutions, and/or chemical derivatives of amino acid residues within the polypeptide sequence. Desired amino acid substitutions (whether conservative or non-conservative) can be determined by those skilled in the art in accordance with guidance provided herein for increasing stability, while maintaining or enhancing potency of the polypeptides. In certain embodiments, conservative amino acid substitutions can encompass non-naturally occurring amino acid residues which are typically incorporated by chemical peptide synthesis rather than by synthesis in biological systems.

Conservative modifications can produce peptides having functional, physical, and chemical characteristics similar to those of the peptide from which such modifications are made. In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an a-helical conformation, (b) the charge or hydrophobicity of the molecule at the target site, or (c) the size of the molecule. For example, a "conservative amino acid substitution" may involve a substitution of a native amino acid residue with a non-native residue such that there is little or no effect on the polarity or charge of the amino acid residue at that position.

Recombinant DNA- and/or RNA-mediated protein expression and protein engineering techniques, or any other methods of preparing peptides, are applicable to the making of the polypeptides disclosed herein or expressing the polypeptides disclosed herein in a target cell or tissue. The term "recombinant" should be understood to mean that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. Examples of such molecular biological procedures are found in Maniatis et al., *Molecular Cloning. A Laboratory Manual*, Cold Spring Harbor Laboratory, Cold Spring Harbor, N.Y., 1982. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The polypeptides can be made in transformed host cells according to methods known to those of skill in the art. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of various embodiments. The selection of a particular host is dependent upon a number of factors, which include, for example, compatibility with the chosen expression vector, toxicity of the polypeptides encoded by the DNA molecule, rate of transformation, ease of recovery of the polypeptides, expression characteristics, bio-safety, and costs. A balance of these factors should be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired polypeptides are expressed. In addition, the DNA optionally further encode, 5' to the coding region of a fusion protein, a signal peptide sequence (e.g., a secretory signal peptide) operably linked to the expressed polypeptide.

The polypeptides can also be made by synthetic methods. Solid phase synthesis can be used as a technique of making individual polypeptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. See, e.g., Merrifield, *Chem. Polypeptides*, Katsoyannis and Panayotis eds., pp. 335-361, 1973; Merrifield, *J. Am. Chem. Soc.* 85:2149, 1963; Davis et al., *Biochem. Intl.* 10:394-414, 1985; Stewart and Young, *Solid Phase Peptide Synthesis*, 1969; U.S. Pat. No. 3,941, 763; Finn et al., *The Proteins*, 3rd ed., 2:105-253, 1976; and Erickson et al., *The Proteins*, 3rd ed., 2:257-527, 1976; "Protecting Groups in Organic Synthesis," 3rd ed., T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000; G. B. Fields et al., Synthetic Peptides: A User's Guide, 77-183, 1990.

A composition that includes a polypeptide covalently linked, attached, or bound, either directly or indirectly through a linker moiety, to another peptide, vehicle (e.g., carrier), or a half-life extending moiety is a "conjugate" or "conjugated" molecule, whether conjugated by chemical means (e.g., post-translationally or post-synthetically) or by recombinant fusion. Conjugation of the polypeptides can be via the N-terminus and/or C-terminus of the polypeptide, or can be intercalary as to the peptide's primary amino acid sequence. Due to the specificity of the polypeptides for cancer cells, the polypeptides can be coupled to other cytotoxic moieties to promote specific delivery to cancer cells and to enhance the cytoxicity of the polypeptides described herein. A linker can be used to create fusion protein(s) that allow introduction of additional moieties to enhance killing or localization of a polypeptide. Specific moieties of interest may include chemotherapeutics, pro-apoptotic factors, targeted therapeutics (e.g., kinase inhibitors, etc.), or other agents that promote killing.

In some embodiments, 1, 2, 3, or 4 polypeptides is/are coupled to or encapsulated in the same or different delivery vehicle, such as a carrier (e.g., a particle), or a liposome. In some embodiments, coupling of the polypeptide(s) to the carrier includes one or more covalent and/or non-covalent interactions. In one embodiment, the carrier is a metallic or polymeric particle. In one embodiment, the carrier is a liposome. The particles can be microscopic or nanoscopic in size. In certain aspects a particle has a diameter of from at least, at most, or about 0.1 μm to at least, at most, or about 10 μm. In another aspect, the particle has an average diameter of at least, at most, or about 0.3 μm to at least, at most, or about 5 μm, 0.5 μm to at least, at most, or about 3 μm, or 0.2 μm to at least, at most, or about 2 μm. In certain aspects the particle can have an average diameter of at least, at most, or about 0.1 μm, or at least, at most, or about 0.2 μm or at least, at most, or about 0.3 μm or at least, at most, or about 0.4 μm or at least, at most, or about 0.5 μm or at least, at most, or about 1.0 μm or at least, at most, or about 1.5 μm or at least, at most, or about 2.0 μm or at least, at most, or about 2.5 μm or at least, at most, or about 3.0 μm or at least, at most, or about 3.5 μm or at least, at most, or about 4.0 μm or at least, at most, or about 4.5 μm or at least, at most, or about 5.0 μm, including all values and ranges there between.

In some embodiments, the charge of a carrier (e.g., positive, negative, neutral) is selected to impart application-specific benefits (e.g., physiological compatibility, beneficial surface-peptide interactions, etc.). In some embodiments, a carrier has a net neutral or negative charge (e.g., to reduce non-specific binding to cell surfaces which, in general, bear a net negative charge). In some instances, a carrier is coupled to multiple polypeptide and can have 2, 3, 4, 5, 6, 7, 8, 9, 10 . . . 20 . . . 50 . . . 100, or more copies of a certain polypeptide or combinations of polypeptides exposed on the surface. In some embodiments, a carrier displays a single type of polypeptide. In some embodiments, a carrier displays multiple different polypeptides on the surface.

The terms "packaged", "encapsulation" and "entrapped," as used herein, refer to the incorporation or association of a polypeptide in or with a liposome or similar vehicle. The polypeptide may be associated with the lipid bilayer or present in the aqueous interior of the liposome, or both.

The liposomes can be formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream. Various types of lipids are used to produce liposomes. For example, amphipathic lipids that find use are zwitterionic, acidic, or cationic lipids. Examples of zwitterionic amphipathic lipids are phosphatidylcholines, phosphatidylethanolamines, sphingomyelins, etc. Examples of acidic amphipathic lipids are phosphatidylglycerols, phosphatidylserines, phosphatidylinositols, phosphatidic acids, etc. Examples of cationic amphipathic lipids are diacyl trimethylammonium propanes, diacyl dimethylammonium propanes, stearylamine, etc. Examples of neutral lipids include diglycerides, such as diolein, dipalmitolein, and mixed caprylin-caprin; triglycerides, such as triolein, tripalmitolein, trilinolein, tricaprylin, and trilaurin; and combinations thereof. Additionally, cholesterol or plant sterols are used in some embodiments, e.g., to make multivesicular liposomes.

A variety of methods are available for preparing liposomes as described in, e.g., Szoka et al., *Ann. Rev. Biophys. Bioeng.* 9:467 (1980), U.S. Pat. Nos. 4,235,871; 4,501,728; and 4,837,028, all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in a suitable solvent, such as tertiary butanol, and then lyophilized to form a more homogeneous lipid mixture that is in a more easily hydrated powder-like form. This film or powder is covered with an aqueous buffered solution and allowed to hydrate, typically over a 15-60-minute period with agitation. The size distribution of the resulting multilamellar vesicles can be shifted toward smaller sizes by hydrating the lipids under more vigorous agitation conditions or by adding solubilizing detergents such as deoxycholate.

Multilamellar liposomes are formed, e.g., by agitation of the dispersion, preferably through the use of a thin-film evaporator apparatus or through shaking or vortex mixing. Unilamellar vesicles are formed by the application of a shearing force to an aqueous dispersion of the lipid solid phase, e.g., by sonication or the use of a microfluidizing apparatus such as a homogenizer or a French press. Shearing force can also be applied using injection, freezing and thawing, dialyzing away a detergent solution from lipids, or other known methods used to prepare liposomes. The size of the liposomes can be controlled using a variety of known techniques including controlling the duration of shearing force.

"Unilamellar liposomes," also referred to as "single lamellar vesicles," are spherical vesicles that include one lipid bilayer membrane that defines a single closed aqueous compartment. The bilayer membrane includes two layers (or "leaflets") of lipids; an inner layer and an outer layer. The outer layer of the lipid molecules is oriented with the hydrophilic head portions toward the external aqueous environment and the hydrophobic tails pointed downward toward the interior of the liposome. The inner layer of the lipid lay directly beneath the outer layer with the lipids oriented with the heads facing the aqueous interior of the liposome and the tails oriented toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments, much like an onion.

II. Expression and Expression Vectors

The nucleic acids encoding any polypeptide(s) described herein can be inserted into or employed with any suitable expression system. Recombinant expression can be accomplished using a vector, such as a plasmid, virus, etc. The vector can include a promoter operably linked to nucleic acid encoding one or more polypeptides. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing nucleic acids encoding proteases can be produced. Such expression vectors include, for example, pET, pET3d, pCR2.1, pBAD, pUC, and yeast vectors. The vectors can be used, for example, in a variety of in vivo and in vitro situations. The vector may be a gene therapy vector, for example an adenovirus vector, a lentivirus vector or a CRISP-R vector.

The expression cassette, expression vector, and sequences in the cassette or vector can be heterologous. As used herein, the term "heterologous" when used in reference to an expression cassette, expression vector, regulatory sequence, promoter, or nucleic acid refers to an expression cassette, expression vector, regulatory sequence, or nucleic acid that has been manipulated in some way. For example, a heterologous promoter can be a promoter that is not naturally linked to a nucleic acid to be expressed, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a protease. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 nucleotides in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the expression constructs.

The expression of one or more protease from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include nucleic acid sequence encoding a marker product. This marker product is used to determine if the gene has been delivered to the cell and once delivered is being expressed. Preferred marker genes are the *E. coli* lacZ gene which encodes B-galactosidase and green fluorescent protein. In some embodiments, the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1:327 (1982)), mycophenolic acid, (Mulligan, R. C. and Berg, P. Science 209:1422 (1980)) or hygromycin, (Sugden, B. et al., Mol. Cell. Biol. 5:410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes or viruses. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff et al., *Science,* 247, 1465-1468, (1990); and Wolff, *Nature,* 352, 815-818, (1991).

For example, the nucleic acid molecule, expression cassette and/or vector encoding a protease can be introduced to a cell by any method including, but not limited to, calcium-mediated transformation, electroporation, microinjection, lipofection, particle bombardment and the like. The cells can be expanded in culture and then administered to a subject, e.g., a mammal such as a human. The amount or number of cells administered can vary but amounts in the range of about 106 to about $10^9$ cells can be used. The cells are generally delivered in a physiological solution such as saline or buffered saline. The cells can also be delivered in a vehicle such as a population of liposomes, exosomes or microvesicles.

The protease can be produced by a transgenic cell that produces exosomes or microvesicles that contain the protease. Exosomes and microvesicles mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., *J Biol Chem.* 286 (16): 14383-14395 (2011); Hu et al., *Frontiers in Genetics* 3 (April 2012); Pegtel et al., *Proc. Nat'l Acad Sci* 107 (14): 6328-6333 (2010); WO/2013/084000; each of which is incorporated herein by reference in its entirety.

Thus, transgenic cells with a heterologous expression cassette or expression vector that expresses one or more protease can be administered to a subject and the exosomes produced by the transgenic cells deliver the protease to a tumor and/or cancer cells in the subject.

In accordance with the above, the present disclosure relates to methods to derive vectors, particularly plasmids, cosmids, viruses and bacteriophages used conventionally in genetic engineering and in gene therapy that comprise a nucleic acid molecule encoding the polypeptide sequence of a protease defined herein. In certain cases, the vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods that are well known to those skilled in the art can be used to construct recombinant vectors. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host.

Another aspect of the invention is directed to a gene therapy vector comprising protease gene construct. Gene therapy vectors are known in the art and include, but are not limited to, lentiviral vectors, adenoviral vectors, adeno-associated viral vectors, plasmids and the like. Construction of a gene therapy vector of the invention can be done by methods known in the art. In certain aspects, a gene therapy vector can be administered in an amount of about, at most, or at least 10, 100, 1000, $1\times10^4$, $1\times10^5$, $1\times10^6$, $1\times10^7$, $1\times10^8$, $1\times10^9$, $1\times10^{10}$, $1\times10^{11}$, $1\times10^{12}$ viral particles (VP) or colony forming units (CFU), including all values and ranges there between. As an example of a gene therapy vector a protease expression cassette can be included in a lentiviral vector. The therapeutic vector can be transduced into cells ex vivo and the cells delivered to the patient. Likewise, a therapeutic vector of the invention can be delivered directly to the patient.

III. Pharmaceutical Formulations and Administration

In certain embodiments, embodiments also provide compositions including 1, 2, 3, 4, 5, 6, 7, or all 8 of (1) eosinophil cationic protein (ECP), (2) human neutrophil elastase (ELANE), (3) cathepsin G (CTSG), (4) proteinase 3 (PRTN3), (5) murine neutrophil elastase (mELANE), (6) murine pancreatic elastase (mELA1), (7) porcine pancreatic elastase (pELA1), (8) rat pancreatic elastase (rELA1/RPE), or variant thereof with one or more of the following: a pharmaceutically acceptable diluent; a carrier; a solubilizer; an emulsifier; and/or a preservative. Such compositions may contain an effective amount of at least one anti-cancer agent or complex. Thus, the use of one or more anti-cancer agents described herein in the preparation of a pharmaceutical composition of a medicament is also included. Such compositions can be used in the treatment of a variety of cancers.

The anti-cancer agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the anti-cancer agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from at least, at most, or about 4.0 to at least, at most, or about 8.5, or alternatively, between at least, at most, or about 5.0 to 8.0, including all values and ranges there between. Pharmaceutical compositions can comprise TRIS buffer of at least, at most, or about pH 6.5-8.5, including all values and ranges there between, or acetate buffer of at least, at most, or about pH 4.0-5.5, including all values and ranges there between, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor (e.g., intratumorally) in question is also contemplated. When administering the compositions by injection, the administration may be by continuous infusion or by single or multiple boluses. For parenteral administration, the anti-metastatic agents may be administered in a pyrogen-free, parenterally acceptable aqueous solution comprising the desired anti-cancer agents in a pharmaceutically acceptable vehicle. A particularly suitable vehicle for parenteral injection is sterile distilled water in which an one or more anti-cancer agents are formulated as a sterile, isotonic solution, properly preserved.

Once the pharmaceutical compositions have been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, at least, at most, or about 0.1% to at least, at most, or about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under GMP conditions.

For the compounds described herein, alone or as part of a pharmaceutical composition, such doses are between at least, at most, or about 0.001 mg/kg and 10 mg/kg body weight, preferably between at least, at most, or about 1 and 5 mg/kg body weight, most preferably between 0.5 and 1 mg/kg body weight, including all values and ranges there between.

Therapeutically effective doses will be easily determined by one of skill in the art and will depend on the severity and course of the disease, the patient's health and response to treatment, the patient's age, weight, height, sex, previous medical history and the judgment of the treating physician.

In some methods, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

The method may further comprise administering to subject a second cancer therapy selected from chemotherapy, radiotherapy, immunotherapy, hormonal therapy (or other targeted therapy), or gene therapy. The method may further comprise administering 1, 2, 3, 4, or all 5 polypeptides or variants thereof to the subject more than once.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, y-irradiation, electron-beam radiation, or microwaves. Moreover, a cell or a patient may be administered a microtubule stabilizing agent, including, but not limited to, taxane, as part of methods. It is specifically contemplated that any of the compounds or derivatives or analogs, can be used with these combination therapies.

In certain aspects, other therapeutic agents useful for combination cancer therapy with the polypeptides described herein include anti-angiogenic agents or angiogenesis inhibitors. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the inhibitors can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Compositions described herein can be combined with signal transduction inhibitors. Examples of such agents include, but are not limited to antibody therapies such as Herceptin (trastuzumab), Erbitux (cetuximab), Yervoy (ipilimumab) and pertuzumab. Examples of such therapies also include, but are not limited to small-molecule kinase inhibitors such as Imatinib (Gleevec), Sunitinib (Sutent), Sorafenib (Nexavar), Erlotinib (Tarceva), Gefitinib (Iressa), Dasatinib (Sprycel), Nilotinib (Tasigna), Lapatinib (Tykerb), Crizotinib (Xalkori), Ruxolitinib (Jakafi), Vemurafenib (Zelboraf), Vandetanib (Caprelsa), Pazopanib (Votrient), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941, BZE235, and others.

Immunotherapy or biological response modifier therapy can be used in combination with the therapies described herein. These treatments use the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), viral vaccines, dendritic cell vaccines, antigen vaccines, anti-idiotype vaccines, DNA vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin).

In certain embodiments passive immunotherapies, such as, naked monoclonal antibody drugs can be used in combination with the polypeptide compositions described herein to treat cancer. Examples of these naked monoclonal antibody drugs include, but are not limited to Rituximab (Rittman), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENA-PAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-a VB3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgGI antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai);

IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Mexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); Orthodone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

In certain embodiments passive immunotherapies, such as, conjugated monoclonal antibodies can be used in combination with the polypeptide compositions described herein to treat cancer. Examples of these conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

In certain embodiments targeted therapies containing toxins can be used in combination with the polypeptide compositions described herein to treat cancer. Targeted therapies containing toxins are toxins linked to growth factors, or in particular embodiments the polypeptides described herein, and do not contain antibodies Some embodiments also include the use of adjuvant immunotherapies in combination with the polypeptide compositions described herein, such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Some embodiments also include the use of hormonal therapies (anti-hormonal agents) in combination with the polypeptide compositions described herein. Anti-hormonal agents include, but are not limited to agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4 (5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Some embodiments include a gene expression modulator. As used herein, a "gene expression modulator" can be an oligonucleotide agent capable of inducing a selective modulation of gene expression in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include regulatory RNA (e.g., virtually any regulatory RNA) such as, but are not limited to antisense oligonucleotides, miRNA, siRNA, RNAi, shRNA, aiRNA, Dicer substrates, aptamers and any analogs or precursors thereof, and HDAC inhibitors such as panobinostat and belinostat.

In some embodiments, the cancer that is administered the composition(s) described herein may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

IV. Antibacterial Compositions and Methods

In another embodiment, the therapeutic compositions can be used as an anti-bacterial polypeptide composition. The prevalence of antibiotic and/or drug resistance in bacteria is becoming one of the leading public health threats. Current antibiotics interfere with the critical biological processes of the pathogens and cause death or growth arrest of the bacteria. As a result, antibiotic therapy exerts a strong selective pressure to favor emergence of antibiotic resistant strains. For that reason, the number of bacteria strains that are resistant to front-line antibiotics is growing at an alarming rate, yet there are no signs of replacement treatments in the market or pipeline. The few alternatives that do exist are either expensive, highly toxic, and/or slow acting. Resistance is even growing among infections that today are considered easily treatable, such as tuberculosis, *salmonella, E. coli*, and gonorrhea.

In some embodiments a polypeptide composition can be used for treating and/or preventing a bacterial infection, such as *Acinetobacter baumannii, Bacillus cereus, Bacillus anthracis, Clostridium botulinum, Clostridium difficile, Clostridium tetani, Clostridium perfringens, Corynebacte-*

*ria diphtheriae, Enterococcus* (e.g., *Streptococcus* D), *Listeria monocytogenes*, Pneumoccocal infections (e.g., *Streptococcus pneumoniae*), Staphylococcal infections and Streptococcal infections; Gram Negative bacteria including *Bacteroides, Bordetella pertussis, Brucella, Campylobacter* infections, enterohaemorrhagic *Escherichia coli* (EHEC/*E. coli* 0157: H7) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulare, Myobacterium johnei, Mycobacterium leprae*, atypical bacteria, *Chlamydia, Mycoplasma, Rickettsia,* Spirochetes, *Treponema pallidum, Borrelia recurrentis, Borrelia* burgdorfii and *Leptospira* icterohemorrhagiae and other miscellaneous bacteria, including *Actinomyces* and *Nocardia*.

Resistant pathogens are especially prevalent in hospitals. Especially dangerous strains such as methicillin-resistant *Staphylococcus aureus* (MRSA). In certain aspects, the polypeptide compositions can be used to treat several healthcare associated (HA) and community associated (CA) strains. HA and CA strains include, but are not limited to ST228, ST239, ST5, ST22, ST45, ST240, ST247, ST250, ST15, ST30, ST36, ST579, ST45, ST59, ST80, ST1: USA400, and ST8: USA300.

Infections caused by certain microorganisms, such as certain gram-negative bacteria are generally unresponsive to present-day antibiotics due to the inability for medicines to penetrate their thicker cell walls. Certain acid-fast bacilli including *Mycobacterium tuberculosis* have also become multi-drug resistant.

The antibacterial compositions can be formulated for administration/use via any suitable route, including but not limited to orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques a intraperitoneally. In preferred embodiments, the compositions are formulated for administration/use as a topical cream, a suspension, an oral formulation, or an intravenous formulation for use as an antibacterial.

The antibacterial composition can be used in conjunction with medical devices to ameliorate or attenuate bacterial infection or contamination. A biomedical device can comprise the polypeptide complex disposed on and/or in the biomedical device. It is contemplated that the polypeptide compositions can be with any biomedical device that is subject to bacterial infection, particularly *S. aureus* and/or *P. aeruginosa* infection. In various non-limiting embodiments, the biomedical device can be a medical implant including but not limited to orthopedic implants (such as fracture-fixation devices, joint prostheses (knee, hip shoulder, etc.), etc.), stents, grafts, shunts, stent grafts, angioplasty devices, vascular catheters, urinary catheters, aortic grafts, balloon catheters, fistulas, wound dressings, dental implants, contact lens sterilization solutions, and any implantable drug delivery device. The compositions can present on the biomedical devices in any suitable amount or arrangement, and may be combined with one or more other components. In one embodiment, the compositions are added together with a polymer coating. In other aspects, the polypeptide complexes used in an anti-bacterial composition. In various non-limiting embodiments, the anti-bacterial compositions can be solid (ex: solid soaps) or liquid (ex: liquid soaps), and may be disposed on a substrate (ex: disinfectant wipes).

Certain aspects provide for methods of treating a bacterial infection comprising administering to subject in need thereof an amount of the polypeptide complex effective to treat the infection. Any subject with a bacterial infection can be treated using the methods.

As used herein, "treating a bacterial infection" means accomplishing one or more of the following: (a) reducing or eliminating infection in the subject; (b) reducing the severity of one or more symptoms of bacterial infection; (c) limiting or preventing development of one or more symptoms of bacterial infection; (d) inhibiting worsening of one or more symptom of bacterial infection; and (e) limiting or preventing recurrence of one or more symptoms of bacterial infection in subjects that were previously symptomatic for the relevant symptom.

Certain aspects are directed to methods for disinfecting a surface, comprising contacting the surface with an anti-bacterial composition. Any suitable surface can be disinfected, including but not limited to counters, sinks, toilets, door handles, desks, medical tools (such as in hospitals, appliances, furniture, beds, etc.).

V. EXAMPLES

The following examples are given for the purpose of illustrating various embodiments and are not meant to limit the embodiments in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, and are not intended as limitations on the scope. Changes therein and other uses which are encompassed within the spirit as defined by the scope of the claims will occur to those skilled in the art.

Example 1

Methods of Treating Cancer

Figure 1:
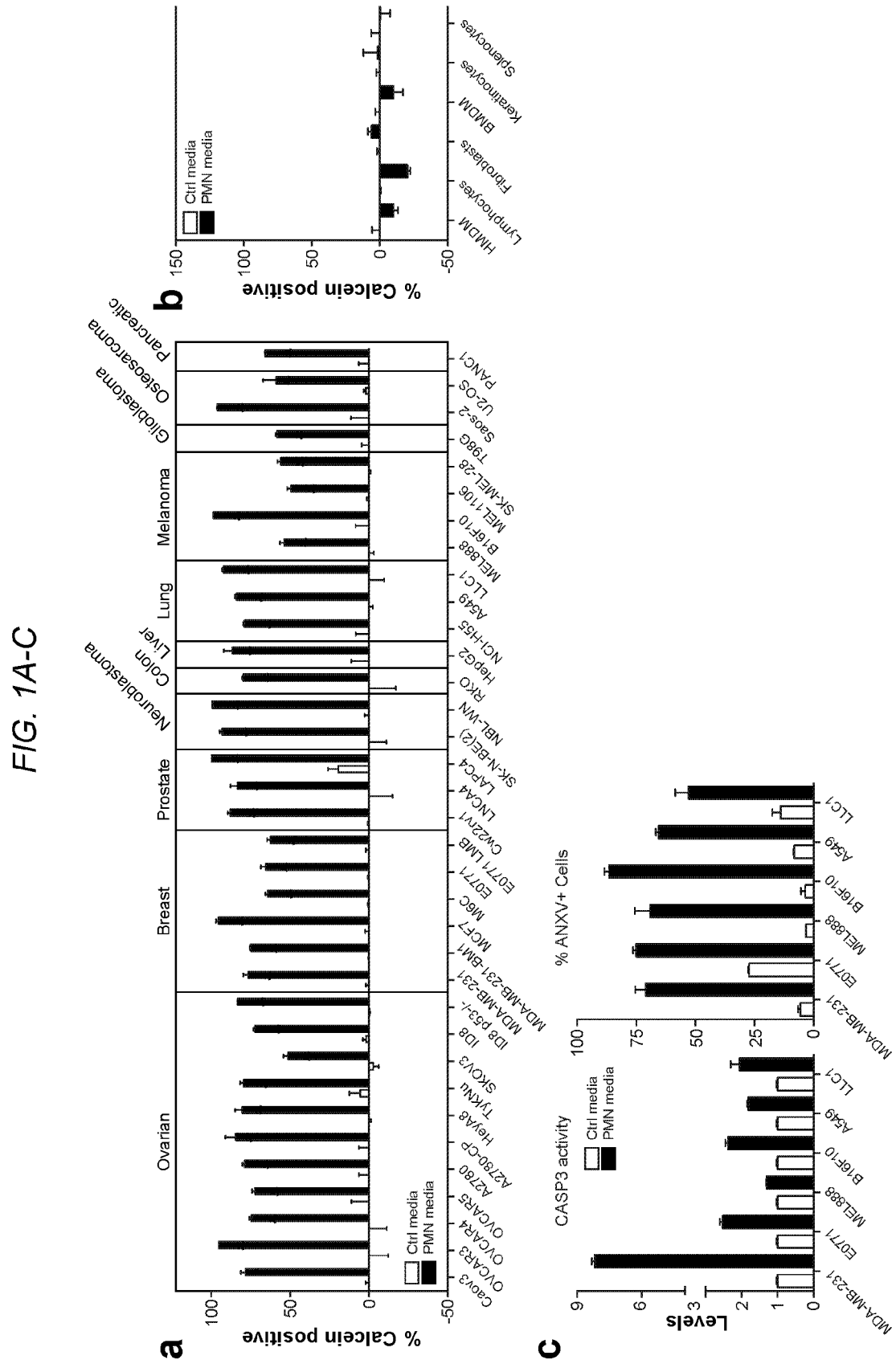
FIG. 1A-C. Human neutrophil-derived factors kill a wide range of cancer cells, without killing normal healthy cells. Human peripheral blood neutrophils (PMN) were isolated from healthy donors and incubated in serum-free DMEM to collect their secreted factors (PMN-media). (a-b) Human or murine cancer cells (a) or healthy cells (b) were incubated with PMN media or control serum-free DMEM (Ctrl media) for 24 hours. Cell viability was assessed by Calcein AM staining. (c) Human or murine cancer cells were treated with PMN media or Ctrl media for 6 hours. Caspase 3/7 activity was examined by a luminescence activity assay, while cell surface Annexin V staining was assessed by flow cytometry. Results showed that PMN media induced cancer cell death through apoptosis. *, p<0.05, Student's t-test.
Figure 2:
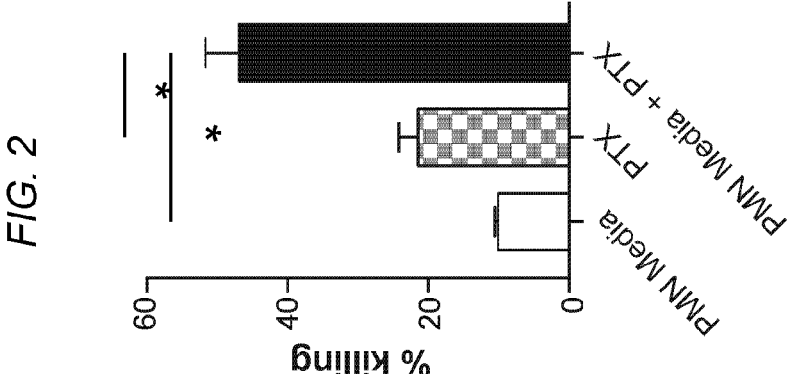
FIG. 2. PMN media synergizes with paclitaxel to kill cancer cells. MDA-MB-231 cells were treated for 6 h with PMN media and paclitaxel (100 nM), alone or in combination. Cell viability was assessed by Calcein AM staining. *, p<0.05, Student's t-test.

Human PMN'S broadly and selectively kill cancer cells. Human peripheral blood neutrophils (PMN) were isolated from healthy donors and incubated in serum-free DMEM to collect their secreted factors (PMN-media). (A-B) Human or murine cancer cells (A) or healthy cells (b) were incubated with PMN media or control serum-free DMEM (Ctrl media) for 24 hours. Cell viability was assessed by Calcein AM staining. (C) Human or murine cancer cells were treated with PMN media or Ctrl media for 6 hours. Caspase 3/7 activity was examined by a luminescence activity assay, while cell surface Annexin V staining was assessed by flow cytometry. Results showed that PMN media induced cancer cell death through apoptosis. *, p<0.05, Student's t-test. (FIG. 1).

Human neutrophil conditioned media kills a broad range of cancer cells. Human peripheral blood neutrophils were isolated from healthy donors. Cells were plated in serum-free DMEM and the neutrophil conditioned media (Neu CM) was collected for 24h. Cancer cells (CAOV3, a human high-grade serous ovarian cancer cell line, is shown as example) were treated with 20 µg/mL Neu CM for 24 h and cancer cell killing was confirmed by Wright-Giemsa staining, Calcein AM, annexin V staining, and caspase-3/7 activity.

Human neutrophil conditioned media is not toxic to non-cancer cells. Human peripheral blood neutrophils were isolated from healthy donors. Cells were plated in serum-free DMEM and the neutrophil conditioned media (Neu CM) was collected for 24h. Non-cancer cells (human monocyte-derived macrophages shown as example) were treated with 100 µg/mL Neu CM for 24 h and the lack of toxicity was confirmed by Wright-Giemsa staining, Calcein AM, annexin V staining, and caspase-3/7 activity.

Figure 3:
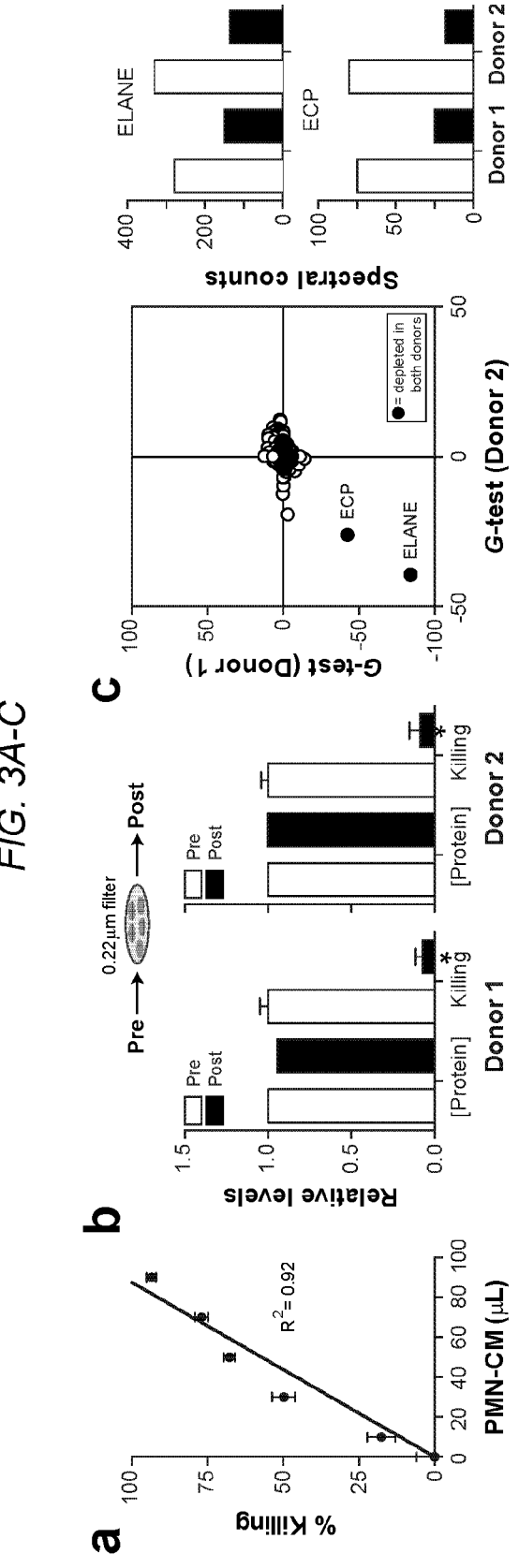
FIG. 3A-C. Proteomics identifies ELANE and ECP as two candidate proteins that mediate the cancer cell killing capability of PMN media. (a) Linear regression analysis (line) showed that killing of MDA-MB-231 cancer cells was well correlated with the dose of PMN media. (b) PMN media was passed through a 0.22 μm filter, and protein concentration and killing activity on MDA-MB-231 cancer cells was measured in both pre- and post-filter solutions. (c) Proteomic analysis identified 890 proteins (≥2 peptides) in PMN media, and only 2 of those were significantly lowered (G-test, p<0.001) by filtration in both donors: neutrophil elastase (ELANE) and eosinophil cationic protein (ECP). ELANE and ECP levels in PMN media pre- and post-filtration were quantified by mass spectrometry (spectral counts).
Figure 4:
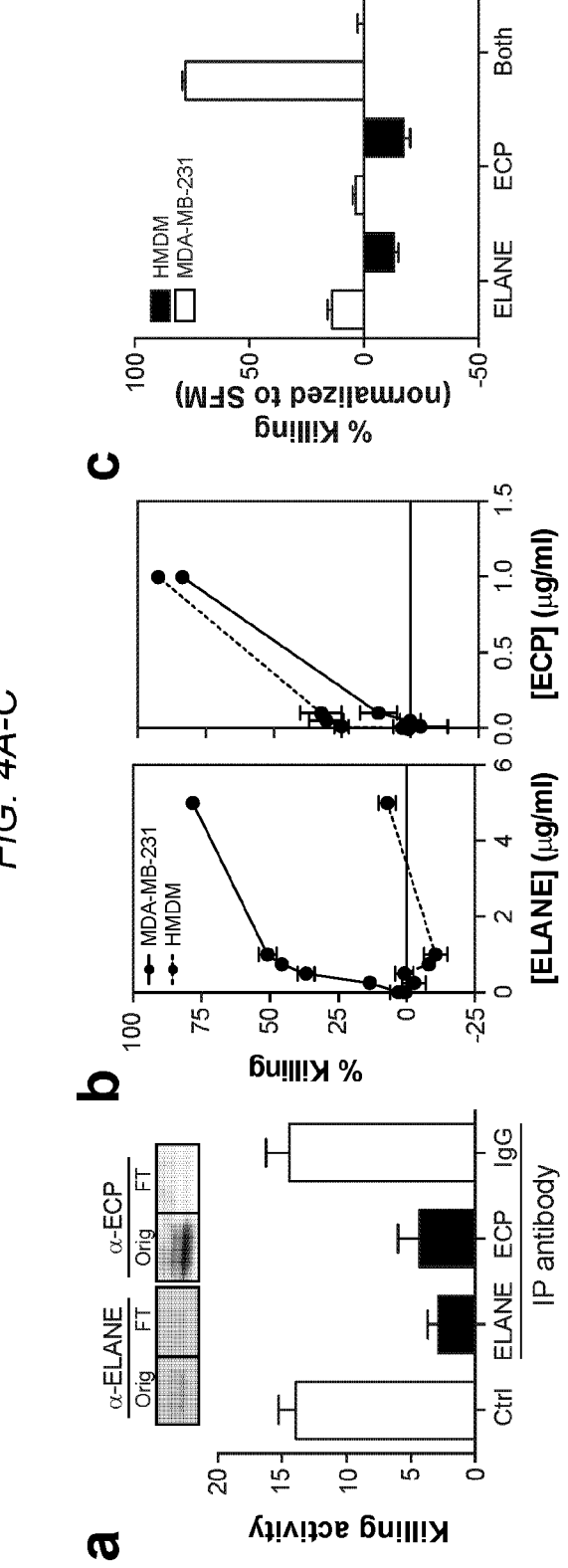
FIG. 4A-C. ELANE and ECP synergize to kill cancer cells. (a) ELANE or ECP were depleted from PMN media by immunoprecipitation; depletion was confirmed by western blotting. MDA-MB-231 cells were treated with depleted media at various dose for 4 hrs, and killing was assessed by Calcein AM. Killing activity was defined as (% cancer cells killed in 4h per volume (uL) of media added)*100. Results show that depleting ELANE or ECP attenuated killing activity in PMN media. PMN media pre-depletion=Orig. and post-depletion=FT. Non-specific IgG was used as a control. (b) MDA-MB-231 cells or human monocyte-derived macrophages (HMDMs) were treated with purified native ELANE or ECP at various doses for 24h, and killing was assessed by Calcein AM staining. (c) MDA-MB-231 cells and HMDMs were treated with levels of ELANE (0.25 ug/mL) or ECP (0.05 ug/mL) that were present in the PMN media, alone or in combination for 24 hrs, and killing was examined by Calcein AM staining. Results show that ELANE and ECP synergize to kill cancer cells, and this mixture is not toxic to non-cancer cells. *, p<0.05, Student's t-test.

Approach to identify the factor(s) mediating selective killing. A quantitative cancer cell killing assay was developed to track the bioactive factor(s). MDA-MB-231 cells were treated with various doses of PMN media and cell viability was assessed by Calcein AM live cells fluorescence staining. (FIG. 3A) Linear regression analysis (line) showed that killing of MDA-MB-231 cancer cells was well correlated with the dose of PMN media. (FIG. 3B) PMN media was passed through a 0.22 µm filter, and protein concentration and killing activity on MDA-MB-231 cancer cells was measured in both pre- and post-filter solutions. (FIG. 3C) Proteomic analysis identified 890 proteins (≥2 peptides) in PMN media, and only 2 of those were significantly lowered (G-test, p<0.001) by filtration in both donors: neutrophil elastase (ELANE) and eosinophil cationic protein (ECP). ELANE and ECP levels in PMN media pre- and post-filtration were quantified by mass spectrometry (spectral counts).

Identification of ECP, ELANE, ANXA6, DEFA1, and CASP3 as candidate cancer cell killing proteins in the neutrophil conditioned media. Neutrophil conditioned media was obtained from 2 different donors (Donor 1 and Donor 2). The inventors found that passing the conditioned media through a 0.2 µm sterile filter eliminated cancer cell killing activity without lowering the total protein concentration. These findings suggested that the 0.2 µm sterile filter specifically depleted cancer cell killing proteins without depleting others. To determine the identity of the proteins depleted by the 0.2 µm sterile filter, the inventors performed quantitative proteomics analysis on the conditioned media from each donor pre- and post-filter. Proteomics analysis identified 2000 proteins, 4 of which (ECP, ELANE, ANXA6, and DEFA1) were depleted in samples from both donors (G-test, p<0.05). The inventors explored the possibility that these proteins might interact with or complement one another. This hypothesis was tested using two approaches. First, the inventors incubated the neutrophil conditioned media with magnetic beads coupled to an anti-ELANE antibody and analyzed the supernatant (sup), wash, and eluent (elute) by western blotting. This analysis identified ECP, DEFA1, and CASP3 as ELANE-binding proteins. Second, the inventors fractionated the neutrophil conditioned media over an anion exchange column (HiTrap Q-sepharose) and found that ELANE, ECP, DEFA1, ANXA6, and CASP3 all co-eluted in the same fraction (fraction 13), which was also the only fraction with cancer cell killing activity.

Immunodepleting ECP, ELANE, ANXA6, DEFA1, or CASP3 from neutrophil conditioned media attenuates cancer cell killing activity. Neutrophil conditioned media was incubated with uncoupled magnetic beads (control) or magnetic beads coupled to anti-ECP, anti-ELANE, anti-ANXA6, anti-DEFA1, or anti-CASP3 antibody. Supernatants from the magnetic beads were collected and tested for their ability to kill MDA-MB-231 cells (a human triple negative breast cancer cell line) by Calcein-AM.

Figure 6:
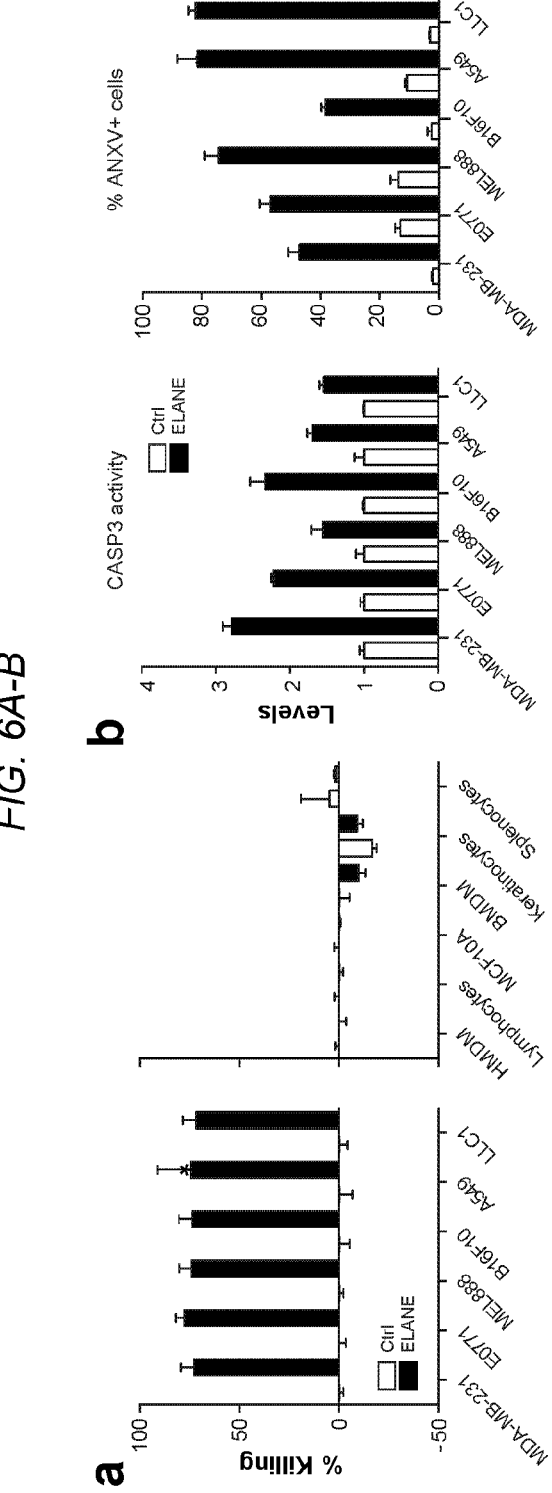
FIG. 6. ELANE kills a wide range of cancer cells, but does not kill normal healthy cells. (a) Cancer cells or healthy cells were treated with 50 nM purified native ELANE or control DMEM media (Ctrl) media for 24 hrs, and cell viability was assessed by Calcein AM staining. (b) Cancer cells were treated with 50 nM ELANE or Ctrl media for 6 hrs, and apoptosis was assessed by Caspase 3/7 luminesce activity assay or cell surface Annexin V staining by flow cytometry. *, p<0.05, Student's t-test.

To determine if ELANE and/or ECP were responsible, the inventors (1) immuno-depleted ELANE or ECP from PMN media; (2) treated cancer or normal cells with purified native ELANE or ECP from commercial sources. (FIG. 6A) ELANE or ECP were depleted from PMN media by immunoprecipitation; depletion was confirmed by western blotting. PMN media pre-depletion=Orig. and post-depletion=FT. Non-specific IgG was used as a control. (FIG. 6B) MDA-MB-231 cells or human monocyte-derived macrophages (HMDMs) were treated with purified native ELANE or ECP at various doses for 24h, and killing was assessed by Calcein AM staining. (FIG. 6C) MDA-MB-231 cells and HMDMs were treated with levels of ELANE (0.25 μg/mL) or ECP (0.05 μg/mL) that were present in the PMN media, alone or in combination for 24 hrs, and killing was examined by Calcein AM staining. Results show that ELANE and ECP synergize to kill cancer cells, and this mixture is not toxic to non-cancer cells. *, p<0.05, Student's t-test.

High doses of ECP or ELANE can kill cancer cells. The inventors sought to determine whether adding purified human ECP (Lee Biosolutions), human ELANE (Abcam), human DEFA1 (Abcam), human ANXA6 (R&D Systems) or human CASP3 (Abcam) individually could kill cancer cells without killing non-cancer cells. Increasing doses of each protein were added to MDA-MB-231 cells for 5h or human monocyte-derived macrophages (HMDMs) for 24 h and cell viability was determined by Calcein-AM. It was found that ECP and ELANE had the highest cancer cell killing activity; DEFA1 had a low amount of activity; while ANXA6 and CASP3 could not kill cancer cells. Only ECP showed toxicity to human monocyte-derived macrophages.

ELANE and ECP synergize to selectively kill cancer cells. MDA-MB-231 and human monocyte-derived macrophages (HMDMs) were treated with levels of ELANE (0.25 μg/mL) or ECP (0.05 μg/mL) that were present in the PMN media, alone or in combination for 24 hrs. killing was examined by Calcein AM staining. Results show that ELANE and ECP synergize to kill cancer cells, and this mixture is not toxic to non-cancer cells.

ELANE selectively kill cancer cells by inducing apoptosis. (FIG. 6A) Cancer cells or healthy cells were treated with 50 nM purified native ELANE or control DMEM media (Ctrl) media for 24 hrs, and cell viability was assessed by Calcein AM staining. (FIG. 6B) Cancer cells were treated with 50 nM ELANE or Ctrl media for 6 hrs, and apoptosis was assessed by Caspase 3/7 luminesce activity assay or cell surface Annexin V staining by flow cytometry. *, p<0.05, Student's t-test.

Combining chemotherapeutics and neutrophil conditioned media enhances the killing of human triple negative breast cancer cells. MDA-MB-231 cells were treated with neutrophil conditioned media (Neu-CM; 4 μg/mL), doxorubicin (DOX; 0.3 μM), or paclitaxel (PTX; 3 nM) for 4h, individually or in combination, and cell viability was assessed by Calcein-AM. It was found that combining doxorubicin or paclitaxel with neutrophil conditioned media enhanced cancer cell killing.

Example 2

Degradation of CD95 and the Treatment of Cancer

Figure 5:
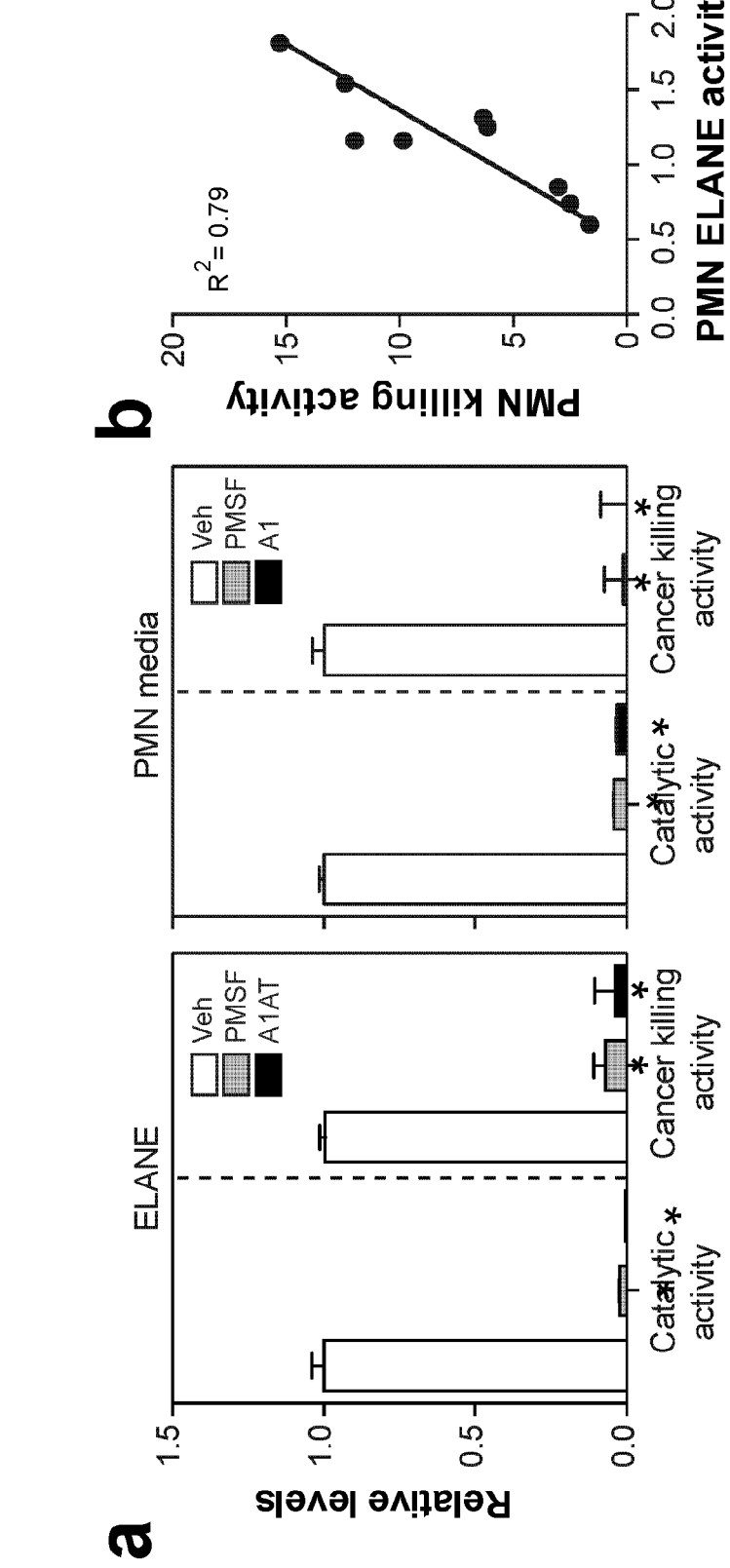
FIG. 5A-B. ELANE is the major bioactive factor in PMN media and its anti-cancer function requires catalytic activity. (a) Purified native ELANE or PMN media was treated with PMSF (100 uM) or alpha-1-anti-trypsin (A1AT; 42 nM) for 30 mins and loss of ELANE catalytic activity was confirmed by a chromogenic substrate assay. Killing assays were performed by treating MIDA-MB-231 cells for 24 hrs treatment and assessed by Calcein AM staining. (b) ELANE activity in PMN media was measured by a chromogenic substrate activity assay, and PMN killing was measured by Calcein AM staining on MDA-MB-231 cells exposed to various dose of PMN media for 4 hrs. Killing activity was defined as (% cancer cells killed in 4h per volume (uL) of media added)*100. Results show that ELANE catalytic activity in PMN media is linearly correlated (line) to the cancer cell killing activity of PMN media from 9 healthy donors. *, p<0.05, Student's t-test.

ELANE catalytic activity is required for its selective cancer cell killing. (FIG. 5A) Purified native ELANE or PMN media was treated with PMSF (100 nM) or alpha-1-anti-trypsin (A1AT; 42 nM) for 30 mins and loss of ELANE catalytic activity was confirmed by a chromogenic substrate assay. Killing assays were performed by treating MDA-MB-231 cells for 24 hrs treatment and assessed by Calcein AM staining. (FIG. 5B) ELANE activity in PMN media was measured by a chromogenic substrate activity assay, and PMN killing was measured by Calcein AM staining on MDA-MB-231 cells exposed to PMN media for 4h. Results show that ELANE catalytic activity in PMN media is linearly correlated (line) to the cancer cell killing capability of PMN media from 9 healthy donors. *, p<0.05, Student's t-test.

Figure 7:
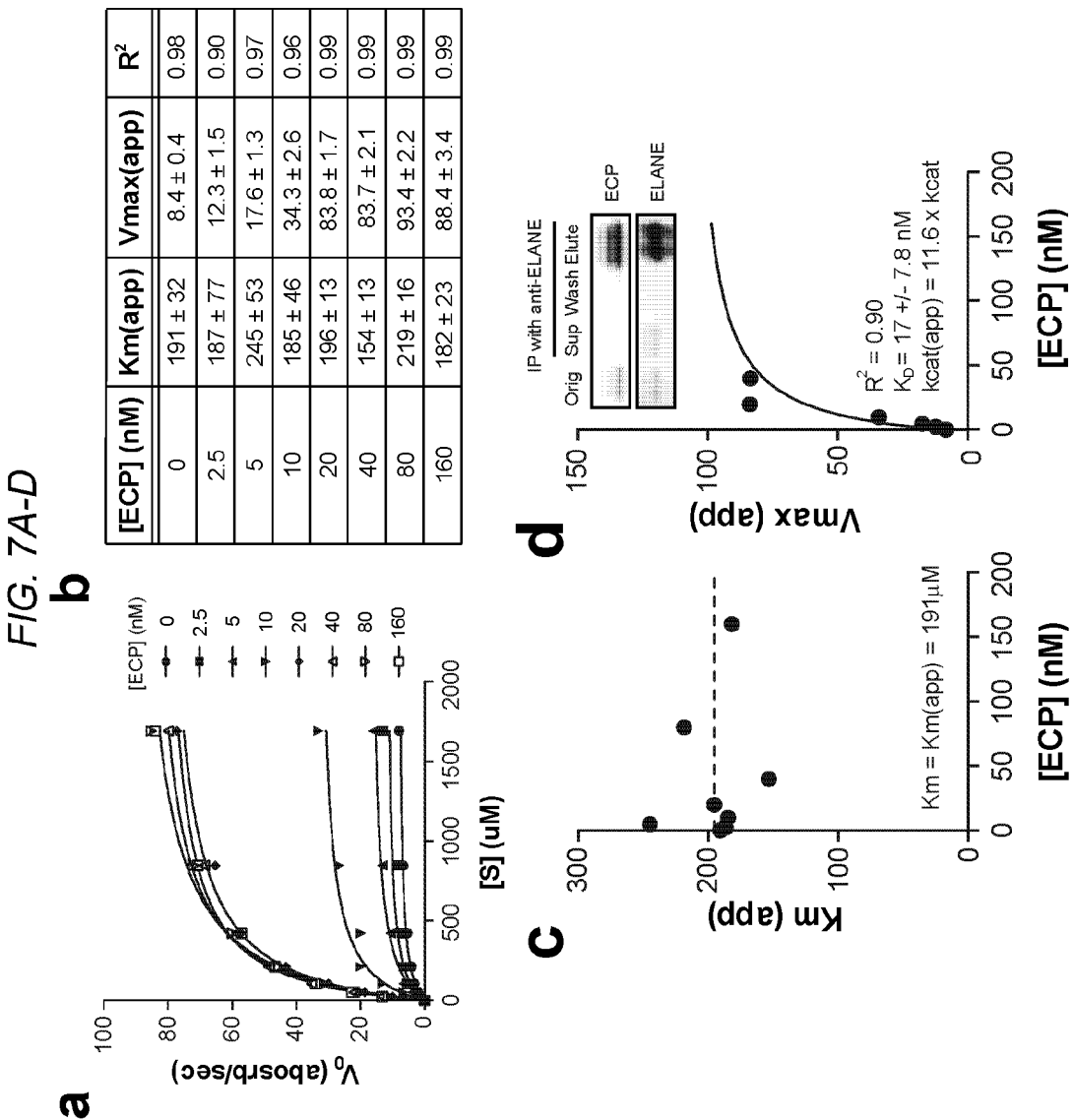
FIG. 7A-D. ECP is a type II allosteric activator of ELANE catalytic activity. (a) 10 nM ELANE was incubated with increasing ECP concentrations at various substrate concentrations. Catalytic activity was measured by a chromogenic substrate activity assay. (b) Km (app) and Vmax (app) values were obtained by fitting curves to Michaelis-Menten equations (lines). (c) Km (app) versus ECP concentration. (d) Vmax (app) versus ECP concentration. ELANE was immunoprecipitated from human PMN media and samples were probed with anti-ELANE and anti-ECP antibodies. Orig=PMN media, Sup=flow-though, Wash=bead wash, Elute=bound to anti-ELANE antibody.

ECP is a type II allosteric activator of ELANE catalytic activity. (FIG. 7A) 10 nM ELANE was incubated with increasing ECP concentrations at various substrate concentrations. Catalytic activity was measured by a chromogenic substrate activity assay. (FIG. 7B) Km (app) and Vmax (app) values were obtained by fitting curves to Michaelis-Menten equations (lines). (FIG. 7C) Km (app) versus ECP concentration. (FIG. 7D) Vmax (app) versus ECP concentration. ELANE was immunoprecipitated from human PMN media and samples were probed with anti-ELANE and anti-ECP antibodies. Orig=PMN media, Sup=flow-though, Wash=bead wash, Elute=bound to anti-ELANE antibody.

Figure 8:
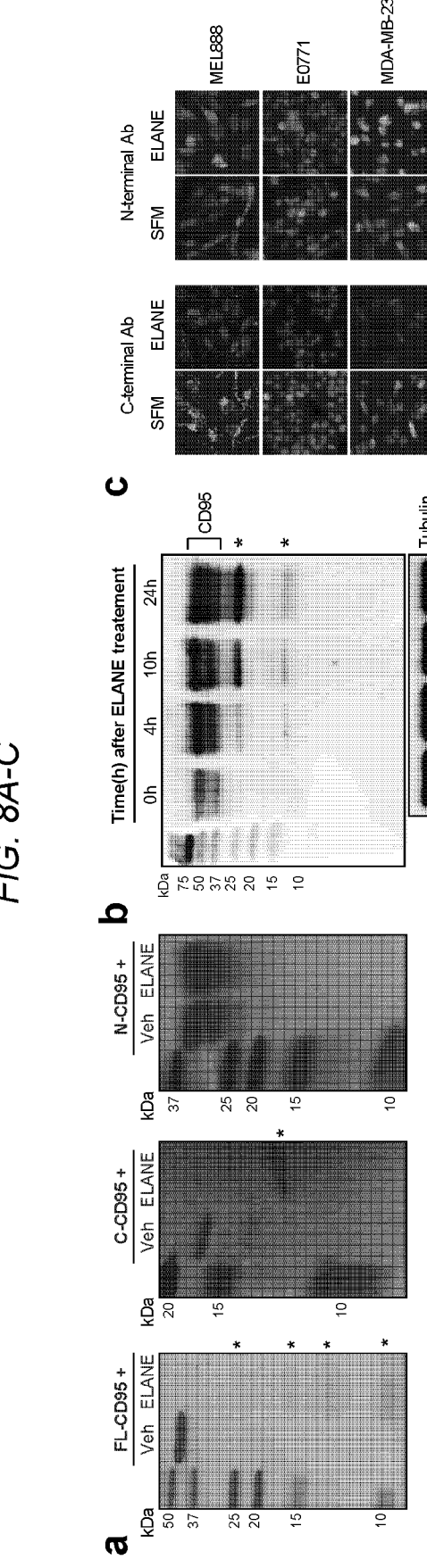
FIG. 8A-C. ELANE treatment results in loss of CD95 immunoreactivity. 157-320; C-CD95) were inbuated with ELANE (0.02 ug) or vehicle (Veh) for 2 hrs at 37° C. Degradation was assessed by SDS-PAGE followed by coomassie blue staining. Results show that ELANE preferentially cleaves the C-terminal domain of CD95 (b) Mel888 cancer cells were treated with ELANE (50 nM) for various times, and CD95 degradation was assessed by western blot analysis with a C-terminal specific anti-CD95 antibody. *, degradation product. (c) Cancer cells were treated with ELANE (50 nM) for 1 hr, fixed in 10% formalin, and stained with N- or C-terminal specific anti-CD95 antibodies (green). Hoechst 33342 solution was used for nuclear staining (blue). Images were taken under 40×. Results show that ELANE-treated cancer cells lose immunoreactivity to a C-terminal specific CD95 antibody, but not to an N-terminal specific CD95 antibody.

ELANE lowers CD95 levels in cancer cells and reduced CD95 levels are associated with apoptosis. (FIG. 8A) Recombinant proteins (1 μg) corresponding to full length CD95 (FL-CD95), N-terminal domain of CD95 (amino acids 1-173; N-CD95), or C-terminal domain of CD95 (amino acids 157-320; C-CD95) were inbuated with ELANE (0.05 μg) or vehicle (Veh) for 2 hrs at 37° C. Degradation was assessed by SDS-PAGE followed by coomassie blue staining. Results show that ELANE preferentially cleaves the C-terminal domain of CD95 (FIG. 8B) Mel888 cancer cells were treated with ELANE (50 nM) for various times, and CD95 degradation was assessed by western blot analysis with a C-terminal specific anti-CD95 antibody. (FIG. 8C) Cancer cells were treated with ELANE (50 nM) for 1 hr, fixed in 10% formalin, and stained with N- or C-terminal specific anti-CD95 antibodies (green). Hoechst 33342 solution was used for nuclear staining (blue). Images were taken under 40×. Results show a that ELANE-treated cancer cells lose immunoreactivity to a C-terminal specific CD95 antibody, but not to an N-terminal specific CD95 antibody. *, degradation product.

ELANE selectively cleaves the C-terminal domain of CD95. The CD95 pathway is essential for the survival of a wide range of cancer cells, but largely dispensable for normal cell survival (Adachi et al., Nat. Genet., 1995; Karray et al., J. Immunol., 2004). CD95 function can be modulated by proteolysis (Strand et al., Oncogene, 2004). To test CD95 involvement in ELANE mediated cell killing ELANE (0.05 μg) was incubated with 1 μg recombinant human C-terminal (aa. 157-320) or N-terminal (aa. 1-173) CD95 for 2 hrs at 37° C. Degradation was assessed by SDS-PAGE followed by staining with coomassie blue. C-terminal domain cleavage. N-terminal domain cleavage. Cancer cells were treated with ELANE (50 nM) for 1 hr, fixed in 10% formalin, and stained with N- or C-terminal specific anti-CD95 antibodies. Hoechst 33342 solution was used for nuclear staining. Images were taken under 40×. Results show the loss of immunoreactivity with a C-terminal specific antibody after ELANE treatment but not N-terminal antibody staining. Mel888 cancer cells were treated with ELANE (50 nM) for various times, and CD95 degradation was assessed by western blot analysis with a C-terminal specific anti-CD95 antibody.

Figure 9:
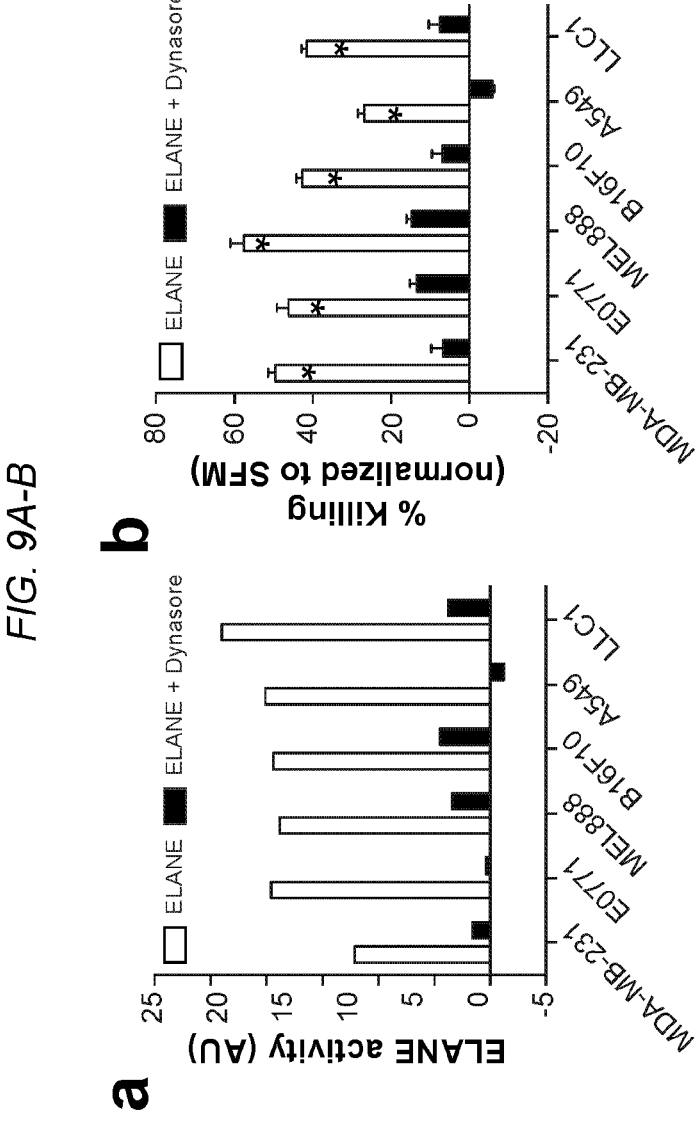
FIG. 9A-B. ELANE uptake by cancer cells is required for its anti-cancer function. (a) Cancer cells were treated with ELANE (100 nM) in the presence or absence of a broad endocytosis inhibitor Dynasore (80 uM) for 30 mins. ELANE catalytic activity in cell lysates was assessed by a chromogenic substrate assay. (b) Cancer cells were treated with ELANE (30 nM) in the presence or absence of Dynasore (80 uM) for 6 hours. Cell viability was examined by Calcein AM staining. *, p<0.05, Student's t-test.

ELANE internalization is required to kill cancer cells. (FIG. 9A) Cancer cells were treated with ELANE (100 nM) in the presence or absence of a broad endocytosis inhibitor Dynasore (80 μM) for 30 mins. ELANE catalytic activity in cell lysates was assessed by a chromogenic substrate assay. (FIG. 9B) Cancer cells were treated with ELANE (30 nM) in the presence or absence of Dynasore (80 μM) for 6 hours. Cell viability was examined by Calcein AM staining. *, p<0.05, Student's t-test.

Figure 10:
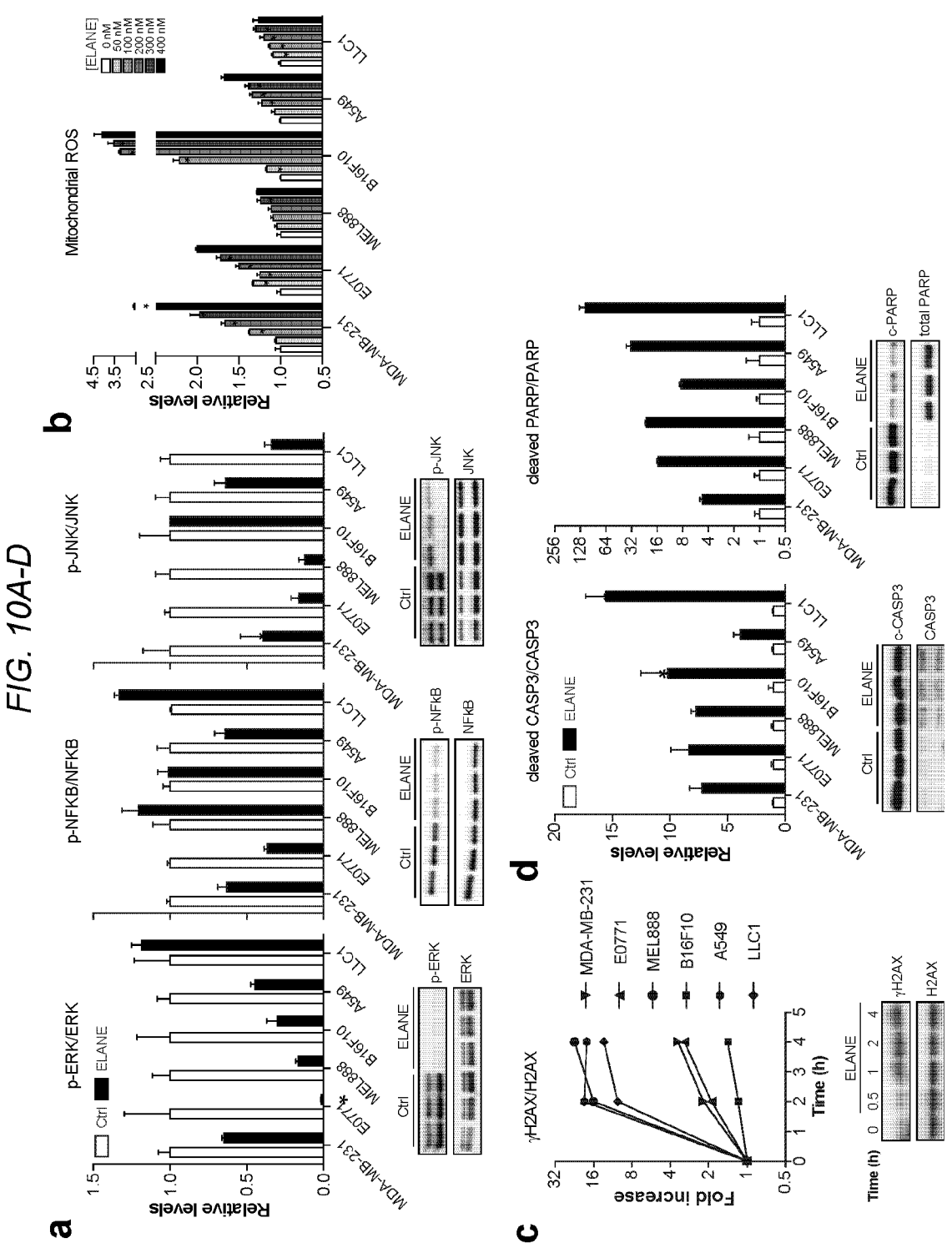
FIG. 10A-D. ELANE induces a robust killing program in cancer cells. (a) Cancer cells were treated with ELANE (50 nM) for 4 hrs, and phosphorylated and total ERK, NFKB, and JNK were quantified by western blotting. Immunoblots for E0771 cancer cells are shown as an example. (b) Cancer cells were treated with various doses of ELANE for 1 hr and mitochondrial ROS was measured by flow cytometry using CM-H2DCFDA dye. (c) Cancer cells were treated with ELANE (50 nM) and DNA damage was assessed by immunoblotting for phospho-(YH2AX) and total H2AX. Immunoblots for A549 cancer cells are shown as an example. (d) Cells were treated with ELANE (50 nM) for 8 hrs, and full length and cleaved CASP3 (c-CASP3) and cleaved PARP (c-PARP) were quantified by immunoblotting. Immunoblots for LLC1 cancer cells are shown as an example. *, p<0.05, Student's t-test.

ELANE induces a robust killing program in cancer cells. (FIG. 10A) Cancer cells were treated with ELANE (50 nM) for 4 hrs, and phosphorylated and total ERK, NFKB, and JNK were quantified by western blotting. Immunoblots for E0771 cancer cells are shown as an example. (FIG. 10B) Cancer cells were treated with various doses of ELANE for 1 hr and mitochondrial ROS was measured by flow cytometry using CM-H2DCFDA dye. (FIG. 10C) Cancer cells were treated with ELANE (50 nM) and DNA damage was assessed by immunoblotting for phospho-(γH2AX) and total H2AX. Immunoblots for A549 cancer cells are shown as an example. (FIG. 10D) Cells were treated with ELANE (50 nM) for 8 hrs, and full length and cleaved CASP3 (c-CASP3) and cleaved PARP (c-PARP) were quantified by immunoblotting. Immunoblots for LLC1 cancer cells are shown as an example. *, p<0.05, Student's t-test.

Figure 11:
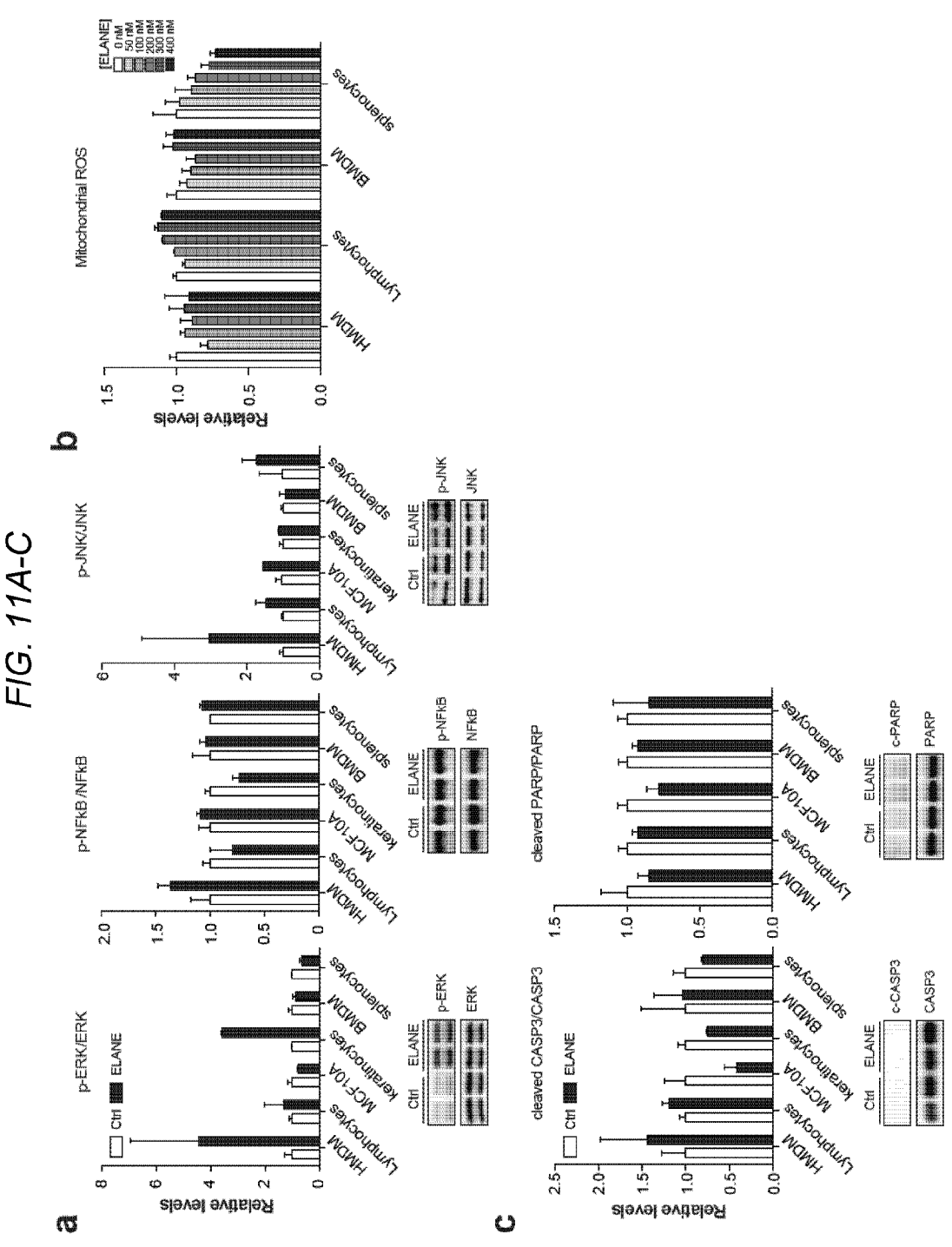
FIG. 11A-C. ELANE does not induce a robust killing program in healthy non-cancer cells. (a) Healthy non-cancer cells were treated with ELANE (50 nM) for 4 hrs, and phosphorylated and total ERK, NFKB, and JNK were quantified by immunoblotting. Immunoblots for BMDMs are shown as an example. (b) Cells were treated with various doses of ELANE for 1 hr and mitochondrial ROS was measured by flow cytometry using CM-H2DCFDA dye. (c) Cells were treated with ELANE (50 nM) for 8 hrs, and full length and cleaved CASP3 (c-CASP3) and cleaved PARP (c-PARP) were quantified by immnoblotting. Immunoblots for BMDMs are shown as an example.

ELANE does not induce a robust killing program in healthy non-cancer cells. (FIG. 11A) Healthy non-cancer cells were treated with ELANE (50 nM) for 4 hrs, and phosphorylated and total ERK, NFKB, and JNK were quantified by immunoblotting. Immunoblots for BMDMs are shown as an example. (FIG. 11B) Cells were treated with various doses of ELANE for 1 hr and mitochondrial ROS was measured by flow cytometry using CM-H2DCFDA dye. (FIG. 11C) Cells were treated with ELANE (50 nM) for 8 hrs, and full length and cleaved CASP3 (c-CASP3) and cleaved PARP (c-PARP) were quantified by immnoblotting. Immunoblots for BMDMs are shown as an example.

Figure 12:
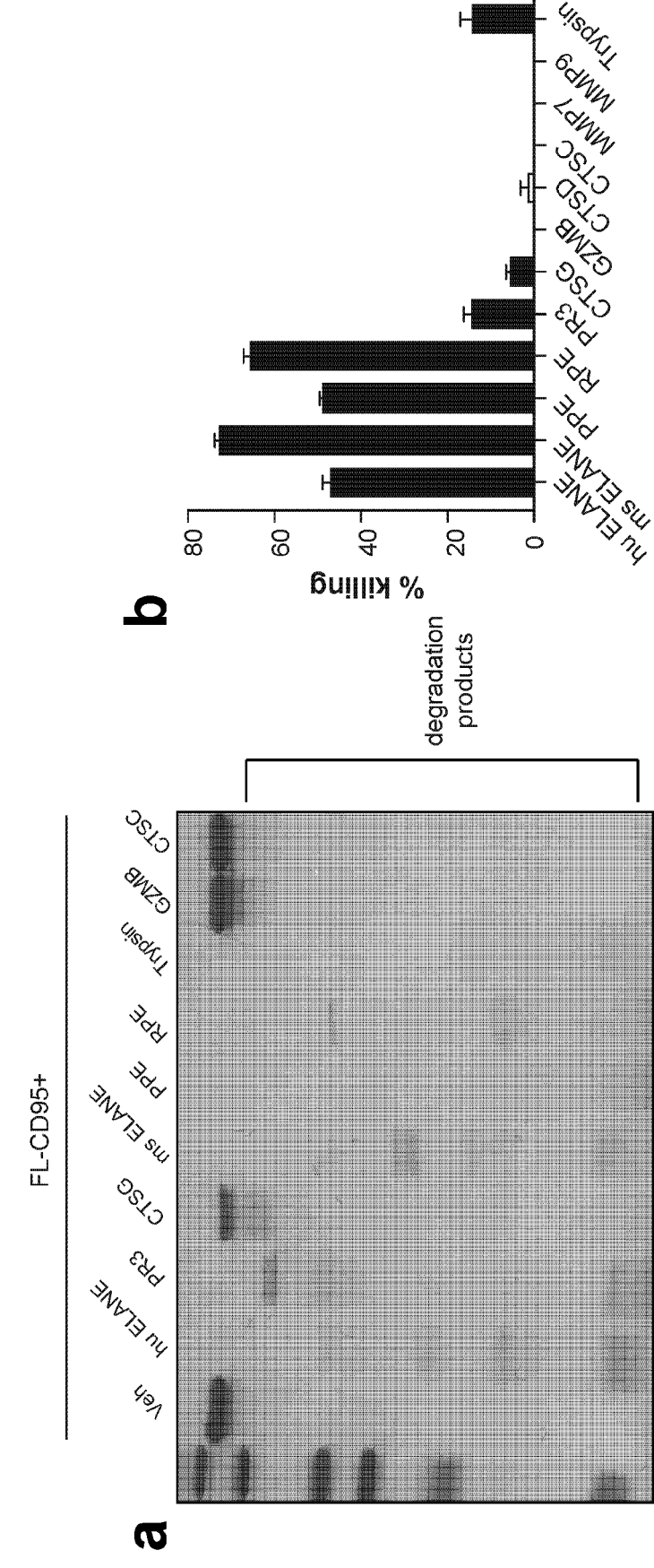
FIG. 12A-B. Capablity of cleaving CD95 predicts the cancer cell killing capability of proteases. (a) Full length recombinanat CD95 protein was incubated with various serine proteases (human ELANE (80 nM), PR3 (80 nM), CSTG (80 nM), PPE (80 nM), mouse ELANE (80 nM), RPE (500 nM), GZMB (80 nM), or Trypsin (250 nM)), or other types of proteases (CTSC (80 nM); or MMP7 (80 nM), MMP9 (80 nM), CTSD (80 nM) not shown) at 37° C. for 2 hours. Degradation was assessed by SDS-PAGE followed by coomassie blue staining. (b) MDA-MB-231 cancer cells were incubated with various proteases for 24 hrs. Cell viability was assessed by Calcein AM staining. PPE: porcine pancreatic elastase. RPE: rat pancreatic elastase.

Other serine proteases cleave the C-terminal domain of CD95, and the ability to cleave the C-terminal domain is associated with cancer cell killing. (FIG. 12A) Full length recombinanat CD95 protein was incubated with various serine proteases (human ELANE (80 nM), PR3 (80 nM), CSTG (80 nM), PPE (80 nM), mouse ELANE (80 nM), rat ELANE (500 nM), GZMB (80 nM), or Trypsin (250 nM)), or other types of proteases (CTSC (80 nM); or MMP7 (80 nM), MMP9 (80 nM), CTSD (80 nM) not shown) at 37° C. for 2 hours. Degradation was assessed by SDS-PAGE followed by coomassie blue staining. (FIG. 12B) MDA-MB-231 cancer cells were incubated with various proteases for 24 hrs. Cell viability was assessed by Calcein AM staining.

Figure 13:
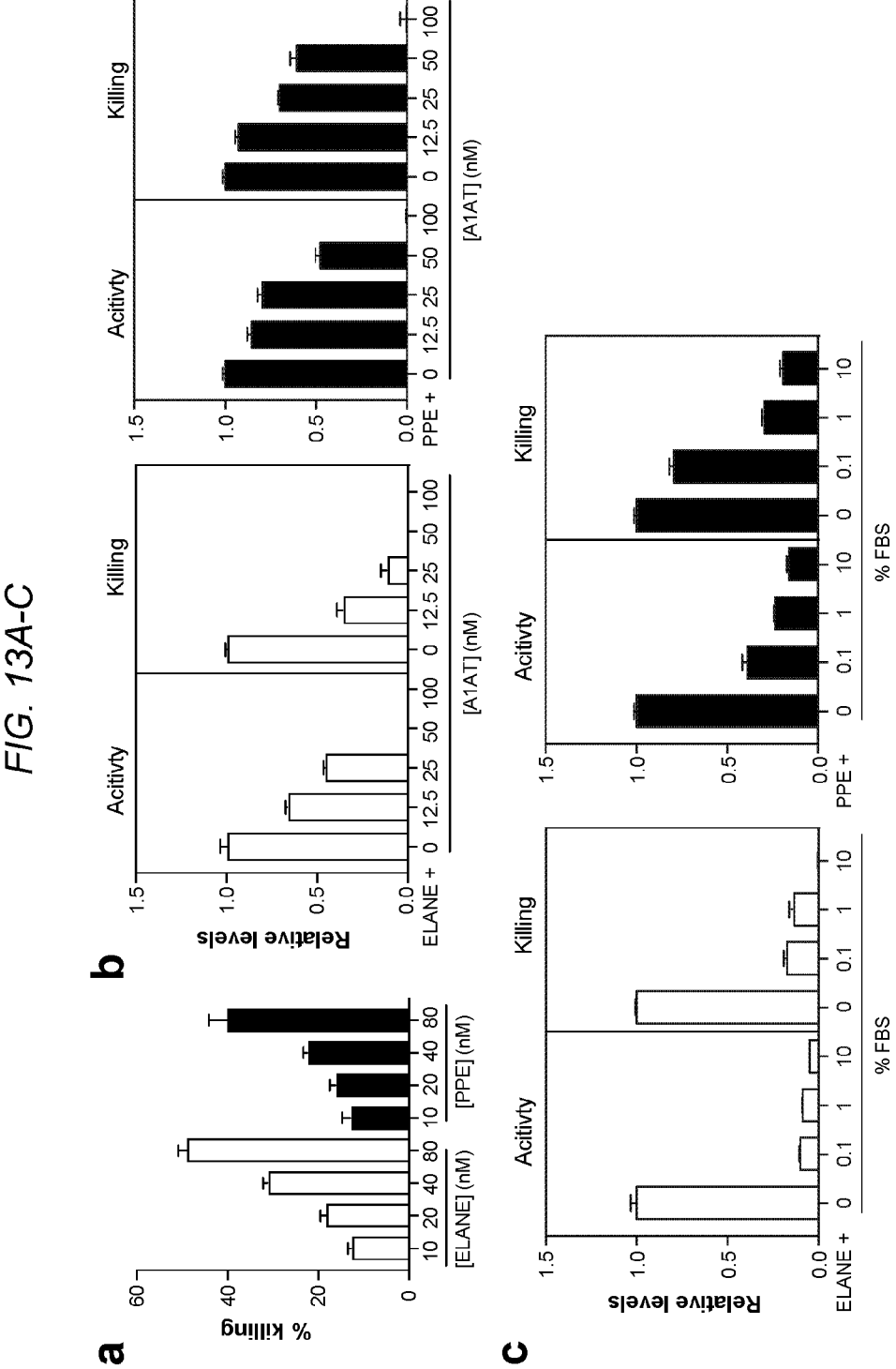
FIG. 13A-C. Porcine pancreatic elastase (PPE) and ELANE are equally toxic to cancer cells, but PPE is more resistant to inhibition by serine protease inhibitors. (a) MDA-MB-231 cancer cells were treated with various doses of purified native ELANE or purified native porcine pancreatic elastase (PPE) for 6h, and killing was assessed by Calcein AM staining. (b). Purified native ELANE or purified native PPE was incubated with different concentrations of alpha-1-anti-trypsin (A1AT) for 15 mins. Catalytic activity was measured using a chromogenic substrate assay. Cancer cell killing capability was determined by treating MDA-MB-231 cancer cells with ELANE or PPE in the presence or absence of A1AT for 6h, followed by Calcein AM staining. (c) Catalytic activity was measured using a chromogenic substrate assay. Cancer cell killing capability was determined by treating MDA-MB-231 cancer cells with ELANE or PPE in the presence or absence of FBS for 6h, followed by Calcein AM staining.

Porcine pancreatic elastase (PPE) and ELANE are equally toxic to cancer cells, but PPE is more resistant to inhibition by serine protease inhibitors. (FIG. 13A) MDA-MB-231 cancer cells were treated with various doses of purified native ELANE or purified native porcine pancreatic elastase (PPE) for 6 h, and killing was assessed by Calcein AM staining. (FIG. 13B). Purified native ELANE or purified native PPE was incubated with different concentrations of alpha-1-anti-trypsin (A1AT) for 15 mins. Catalytic activity was measured using a chromogenic substrate assay. Cancer cell killing capability was determined by treating MDA-MB-231 cancer cells with ELANE or PPE in the presence or absence of A1AT for 6h, followed by Calcein AM staining. (FIG. 13C) Catalytic activity was measured using a chromogenic substrate assay. Cancer cell killing capability was determined by treating MDA-MB-231 cancer cells with ELANE or PPE in the presence or absence of FBS for 6 h, followed by Calcein AM staining.

ELANE induces a robust killing program in a variety of cancer cells. Human and mouse cancer cells were treated with ELANE and signaling pathways associated with cancer cell death were assessed. Cells were treated with ELANE (50 nM) for 4 hrs, and phosphorylated and total ERK, NFKB, and JNK were quantified by western blotting. Cells were treated with various doses of ELANE for 1 hr and mitochondrial ROS was measured by flow cytometry using CM-H2DCFDA dye. Cells were treated with ELANE (50 nM) and DNA damage was assessed by western blot for phospho-(γH2AX) and total H2AX. Cells were treated with ELANE (50 nM) for 8 hrs, and full length and cleaved CASP3 and PARP were quantified by western blotting.

Catalytically active ELANE is internalized by non-cancer cells, resulting in loss of immunoreactivity with a C-terminal specific antibody. Non-cancer cells were treated with ELANE (50 nM) for 1 hr, fixed in 10% formalin, and stained with N- or C-terminal specific anti-CD95 antibodies. Hoechst 33342 solution was used for nuclear staining. Images were taken under 40×. Results show the loss of immunoreactivity with a C-terminal specific antibody after ELANE treatment but not N-terminal antibody staining. Non-cancer cells were treated with ELANE (100 nM) in the presence or absence of a broad endocytosis inhibitor Dynasore (80 μM) for 30 mins. ELANE catalytic activity in cell lysates was assessed using a chromogenic substrate assay.

The ELANE-induced killing program is not observed in non-cancer cells. Human and mouse non-cancer cells were treated with ELANE and signaling pathways associated with cancer cell death were assessed. Cells were treated with ELANE (50 nM) for 4 hrs, and phosphorylated and total ERK, NFKB, and JNK were quantified by western blotting. Cells were treated with various doses of ELANE for 1 hr and mitochondrial ROS was measured by flow cytometry using CM-H2DCFDA dye. Cells were treated with ELANE (50 nM) for 8 hrs, and full length and cleaved CASP3 and PARP were quantified by western blotting.

Figure 14:
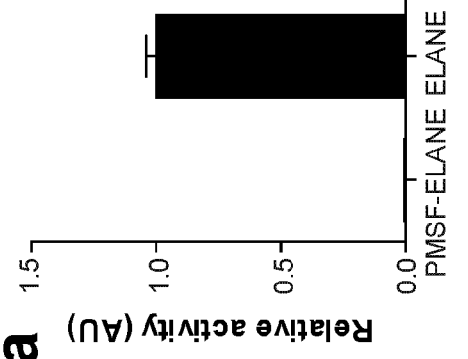
FIG. 14A-B. Catalytically active ELANE attenuates tumor growth. (a) Catalytic activity of ELANE or ELANE that had been inactivated by treatment with 1 mM PMSF (PMSF-ELANE) was determined by a chromogenic substrate. (b) E0771, B16F10, or LLC1 cancer cells were injected into C57BL/6 mice. Once tumors reached ~100 mm3, human serum albumin (HSA, 11.6 ug), ELANE (11.6 ug), or PMSF-ELANE (11.6 ug) were delivered intratumorally once/day for 5 days. Tumor volume was assessed by calipers. Results show that active ELANE slows tumor growth, whereas PMSF-ELANE has no effect on tumor growth.

ELANE activity is required for its anti-tumor function in vivo. (FIG. 14A) Catalytic activity of ELANE or ELANE that had been inactivated by treatment with 100 nM PMSF (PMSF-ELANE) was determined by a chromogenic substrate. (FIG. 14B) E0771, B16F10, or LLC1 cancer cells were injected into C57BL/6 mice. Once tumors reached ~100 mm³, human serum albumin (HSA, 11.6 μg), ELANE (11.6 μg), or PMSF-ELANE (11.6 μg) were delivered intratumorally once/day for 5 days. Tumor volume was assessed by calipers. Results show that active ELANE slows tumor growth, whereas PMSF-ELANE has no effect on tumor growth.

Figure 15:
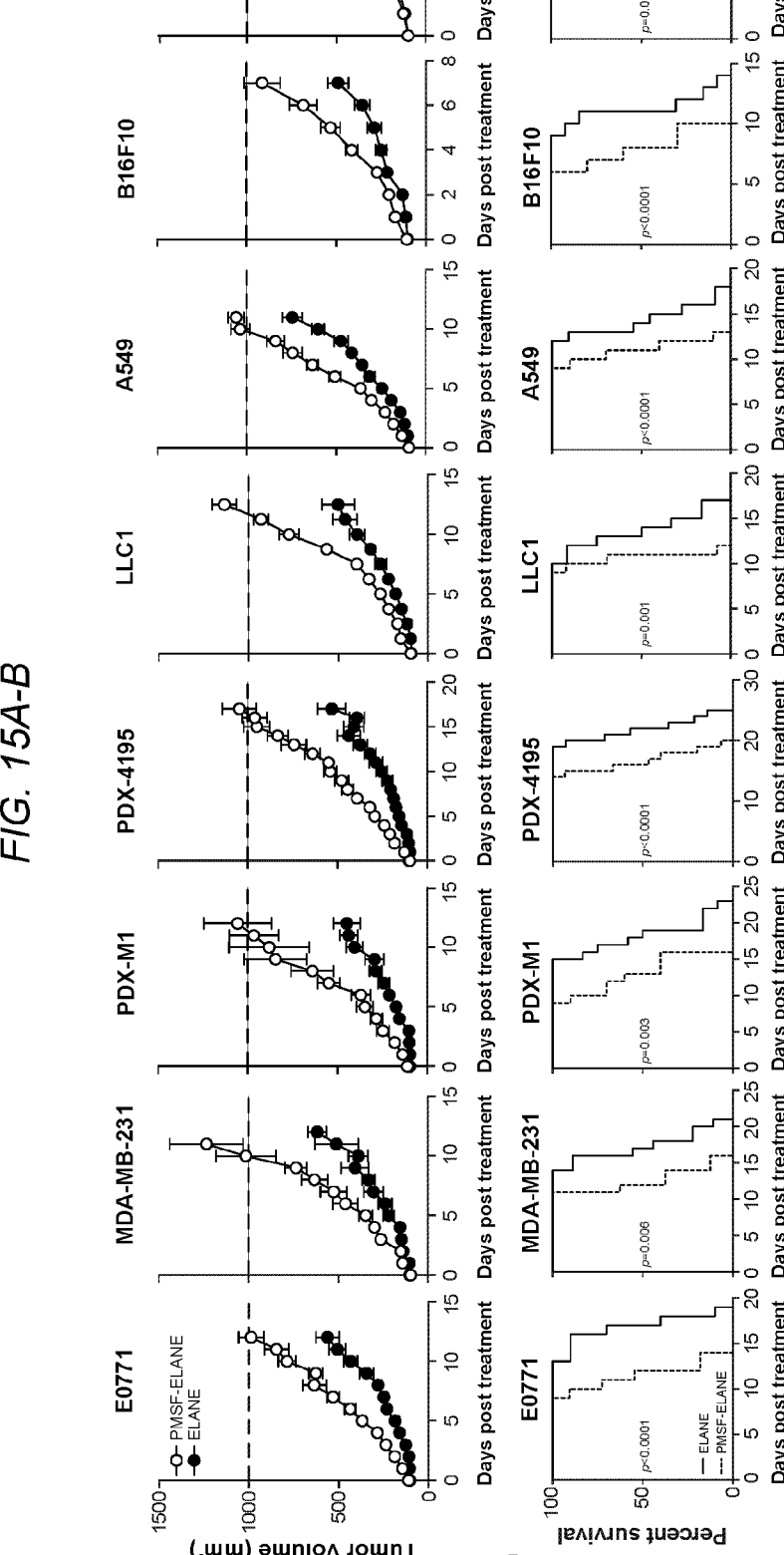
FIG. 15A-B. Intra-tumorally delivered ELANE attenuates tumor growth in many cancer models. MDA-MB-231, A549, or MEL888 cells (xenograft model) were injected into athymic nude mice; M1 or 4195 tumors (TNBC PDX models) were propagated in SCID mice; and E0771, LLC1, or B16F10 cells (syngeneic models) were injected into C57BL/6 mice. Once tumors reached ~100 mm3, ELANE (11.6 ug), or PMSF-ELANE (11.6 ug) were delivered intratumorally once/day for 5 days. n=8-15 mice/group. Tumor volume was assessed by calipers (a). Kaplan-Meier curve was plotted and the logrank test (Mentel-Cox method) was used for mouse survival analysis (b). Day 0 refers to the first treatment day. End point of survival is defined as tumor volume >1000 mm$^3$.

Intra-tumorally delivered ELANE attenuates tumor growth in many cancer models. MDA-MB-231, A549, or MEL888 cells (xenograft model) were injected into athymic nude mice; M1 or 4195 tumors (TNBC PDX models) were propagated in SCID mice; and E0771, LLC1, or B16F10 cells (syngeneic models) were injected into C57BL/6 mice. Once tumors reached ~100 mm³, ELANE (11.6 μg), or PMSF-ELANE (11.6 μg) were delivered intratumorally once/day for 5 days. n=8-15 mice/group. Tumor volume was assessed by calipers. Kaplan-Meier curve was plotted and the logrank test (Mentel-Cox method) was used for mouse survival analysis. Day 0 refers to the first treatment day. End point of survival is defined as tumor volume >1000 mm³. (FIG. 15)

Figure 16:
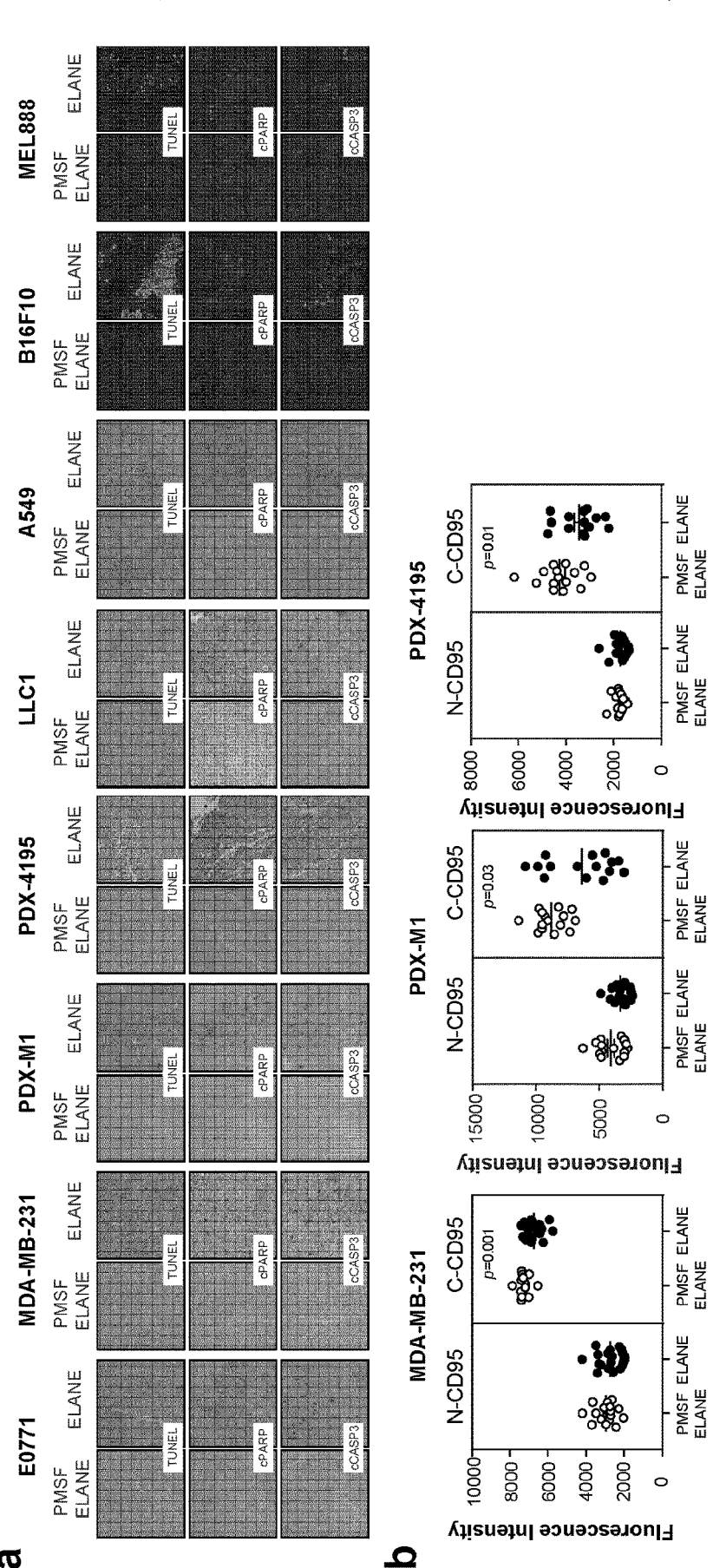
FIG. 16A-B. Intra-tumorally delivered ELANE induces cancer cell apoptosis. (a) MDA-MB-231, A549, or MEL888 (xenograft model) cells were injected into athymic nude mice; M1 or 4195 tumors (TNBC PDX models) were propagated in SCID mice; and E0771, LLC1, or B16F10 cells (syngeneic models) were injected into C57BL/6 mice. Once tumors reached ~100 mm$^3$, ELANE (11.6 ug), or PMSF-ELANE (11.6 ug) were delivered intratumorally once/day for 5 days. Tumors were isolated on day 6, formalin fixed, and examined by immunohistochemistry or immunofluorescence staining for TUNEL, cleaved-PARP (cPARP), and cleaved CASP3 (cCASP3). Images were taken under 40×. (B) Tumor sections were stained with N-terminal (N-CD95) and C-terminal (C-CD95) specific anti-CD95 antibodies, followed by secondary antibody staining (Alex fluor 488 and 594 for C-CD95 and N-CD95 respectively). Fluorescence intensity quantification was performed on 3-4 areas/mouse. Results show that ELANE treatment attenuates C-CD95 levels in vivo. *, p<0.05, Student's t-test.

Intra-tumorally delivered ELANE induces cancer cell apoptosis. (FIG. 16A) MDA-MB-231, A549, or MEL888

(xenograft model) cells were injected into athymic nude mice; M1 or 4195 tumors (TNBC PDX models) were propagated in SCID mice; and E0771, LLC1, or B16F10 cells (syngeneic models) were injected into C57BL/6 mice. Once tumors reached ~100 mm³, ELANE (11.6 μg), or PMSF-ELANE (11.6 μg) were delivered intratumorally once/day for 5 days. Tumors were isolated on day 6, formalin fixed, and examined by immunohistochemistry or immunofluorescence staining for TUNEL, cleaved-PARP (cPARP), and cleaved CASP3 (cCASP3). Images were taken under 40×. (FIG. 16B) Tumor sections were stained with N-terminal (N-CD95) and C-terminal (C-CD95) specific anti-CD95 antibodies, followed by secondary antibody staining (Alex fluor 488 and 594 for C-CD95 and N-CD95 respectively). Fluorescence intensity quantification was performed on 3-4 areas/mouse. Results show that ELANE treatment attenuates C-CD95 levels in vivo. *, p<0.05, Student's t-test.

ELANE does not produce evident side-effects in healthy non-tumor bearing mice. 4 μM human albumin (Ctrl) or 4 μM ELANE was injected into the mammary fat pad of healthy non-tumor-bearing C57BL/6 mice once a day for 5 consecutive days, and side effects were monitored. Body weight, spleen weight, and blood ALT activity levels (a marker of liver function). Immunohistochemistry staining for apoptosis markers (cleaved CASP3 (c-CASP3), cleaved PARP (c-PARP)) 2 days after the final injection. Quantification of CD8+ effector cytotoxic T-cells (defined as $CD3^+ CD8^+ CD62L^{LO} CD44^{HI}$) in the blood 2 days after the final injection.

ELANE treatment in immune competent mice was more efficacious than adaptive immunity deficient mice. The rationale is based on the observation that therapeutics that kill cancer cells in vivo have been shown to increase adaptive immune responses. The inventors therefore explored whether ELANE-mediated cancer cell killing could positively influence the immune cells in the tumor. $Rag2^{-/-}$ mice in C57BL/6 background (no adaptive immunity) and wild type (wt) C57BL/6 mice were both ordered from the Jackson laboratory. E0771 cancer cells were injected into both mouse models. Once tumors reached ~100 mm³. ELANE (11.6 μg) or HAS (11.6 μg) were delivered intratumorally once/day for 5 days. Tumor volume was assessed by calipers. Kaplan-Meier curve was plotted and the logrank test (Mentel-Cox method) was used for mouse survival analysis. End point of survival is defined as tumor volume >1000 mm³.

Figure 17:
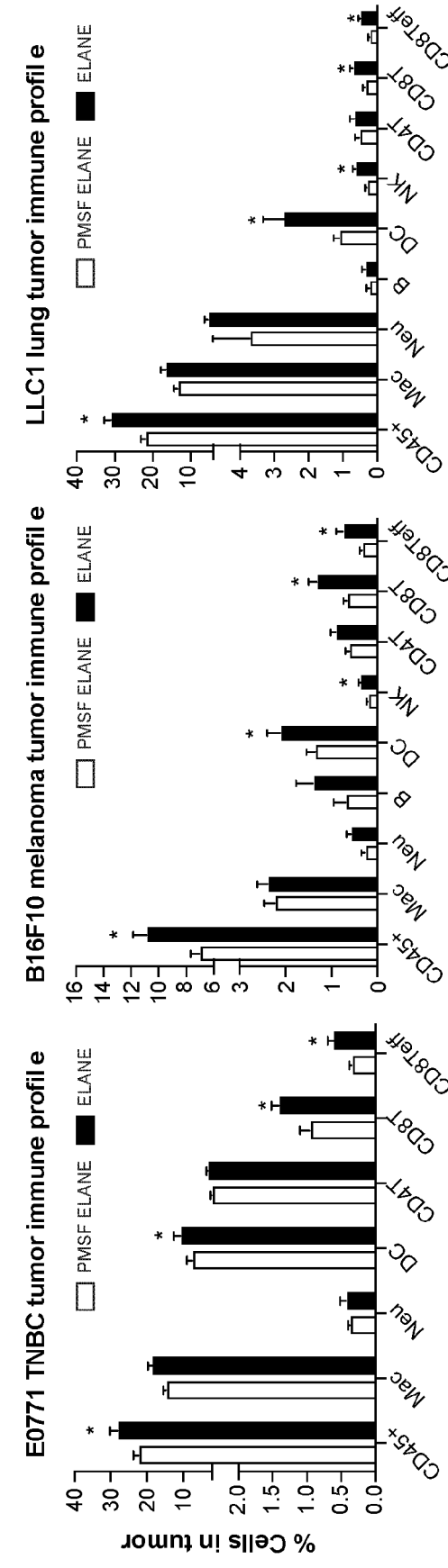
FIG. 17. Intra-tumorally delivered ELANE increases tumoral immune cells. E0771, B16F10, or LLC1 cancer cells were injected into C57BL/6 mice. Once tumors reached ~100 mm$^3$, ELANE (11.6 ug) or PMSF-ELANE (11.6 ug) were delivered intratumorally once/day for 5 days. Tumors were isolated on day 6 and digested for immune cell analysis by flow cytometry. CD45+ cells are the total immune cells; macrophages (Mac) are defined as CD45+CD11b+CD11c$^{low}$MHCII$^{low}$, neutrophils (Neu) are defined as CD45+CD11b+Ly6G+, dendritic cells (DC) are defined as CD45+CD11b+CD11c$^{high}$MHCII$^{high}$, B cells (B) are defined as CD45+B220+, NK cells (NK) are defined as CD45+NK1.1+CD16+, CD4+ T cells (CD4T) are defined as CD3+CD4+CD8−, CD8+ T cells (CD8T) are defined as CD3+CD8+CD4−, CD8 effector T cells (CD8Teff: including effector memory) are defined as CD3+CD8+CD4-CD62L$^{low\ and\ high}$CD44+. *, p<0.05, Student's t-test.

Intra-tumorally delivered ELANE increases tumoral immune cells. E0771, B16F10, or LLC1 cancer cells were injected into C57BL/6 mice. Once tumors reached ~100 mm³, ELANE (11.6 μg) or PMSF-ELANE (11.6 μg) were delivered intratumorally once/day for 5 days. Tumors were isolated on day 6 and digested for immune cell analysis by flow cytometry. CD45+ cells are the total immune cells; macrophages (Mac) are defined as CD45+CD11b+CD11c$^{low}$MHCII$^{low}$, neutrophils (Neu) are defined as CD45+CD11b+Ly6G+, dendritic cells (DC) are defined as CD45+CD11b+CD11c$^{high}$MHCII$^{high}$, B cells (b) are defined as CD45+B220+, NK cells (NK) are defined as CD45+NK1.1+CD16+, CD4+ T cells (CD4T) are defined as CD3+CD4+CD8−, CD8+ T cells (CD8T) are defined as CD3+CD8+CD4−, CD8 effector T cells (CD8Teff) are defined as CD3+CD8+CD4−CD62L−CD44+. *, p<0.05, Student's t-test. (FIG. 17)

Figure 18:
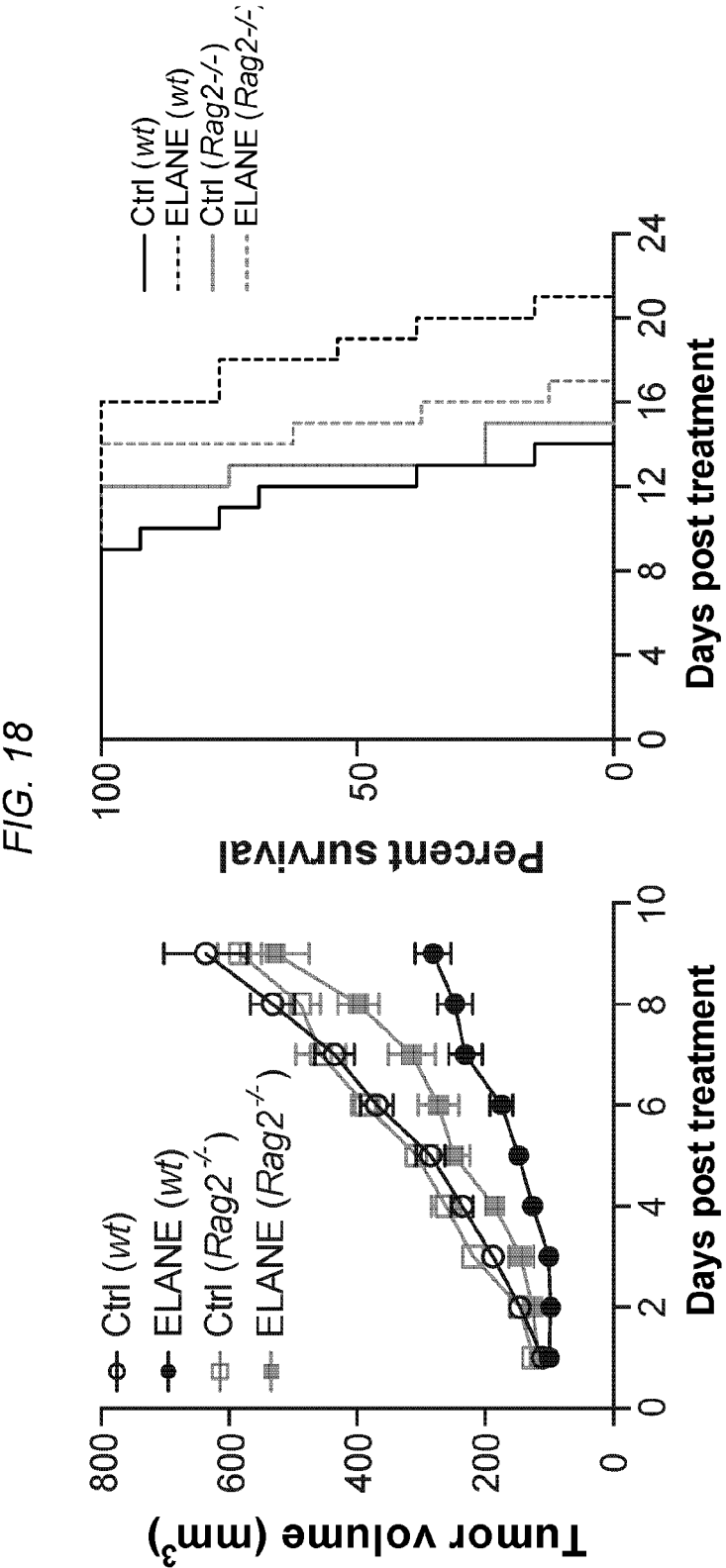
FIG. 18. Adaptive immune cells contribute to ELANE's therapeutic efficacy. Rag2-deficient (Rag2−/−) mice on the C57BL/6 background (no adaptive immunity) and wild type (wt) C57BL/6 mice were injected with E0771 cancer cells. Once tumors reached ~100 mm$^3$. ELANE (11.6 μg) or HSA (11.6 μg) were delivered intra-tumorally once/day for 5 days. (a) Tumor volume was assessed by calipers. (B) Kaplan-Meier curve was plotted and the logrank test (Mentel-Cox method) was used for survival analysis. End point of survival is defined as tumor volume >1000 mm³.

Adaptive immune cells contribute to ELANE's therapeutic efficacy. Rag2-deficient (Rag2−/−) mice on the C57BL/6 background (no adaptive immunity) and wild type (wt) C57BL/6 mice were injected with E0771 cancer cells. Once tumors reached ~100 mm³. ELANE (11.6 μg) or HSA (11.6 μg) were delivered intra-tumorally once/day for 5 days. (FIG. 18A) Tumor volume was assessed by calipers. (FIG. 18B) Kaplan-Meier curve was plotted and the logrank test (Mentel-Cox method) was used for survival analysis. End point of survival is defined as tumor volume >1000 mm³.

Intra-tumorally delivered ELANE induces an abscopal effect. (FIG. 19A) E0771 cancer cells were injected into left (0.5 million cells) and right (0.4 million cells) mammary fat pad of C57BL/6 mice. Once tumors on the left side reached ~100 mm³, ELANE (11.6 μg) or PMSF-inactivated ELANE (PMSF-ELANE) were injected intra-tumorally into the left tumor once/day for 5 days. n=10 mice/group. No action was performed on the right side of the tumor (abscopal side). Tumor volume on both sides were measured by calipers. (FIG. 19B) To eliminate the possibility that the abscopal effect was due to spillover of ELANE from the left to the right tumor, E0771 cancer cells were injected only into the left mammary fat pad of C57BL/6 mice, and mice were treated daily with ELANE (11.6 μg) or PMSF-ELANE into the right mammary fat pad. Tumor volume was measured by calipers. Results show that ELANE does not lower tumor growth when it is injected to the contralateral (non-tumor bearing) mammary fat pad.

Intra-tumorally delivered ELANE enables anti-PDL1 efficacy in a mouse model of TNBC. E0771 cancer cells were injected into C57BL/6 mice. Once tumors reached ~100 mm³, mice were randomly separated into four groups: ELANE (11.6 μg), PMSF-inactivated ELANE (PMSF-ELANE), anti-PD-L1 (BioXCell, 10F.9G2, 100 μg), and ELANE (11.6 μg)+anti-PD-L1 (100 μg). n=8-9 mice/group. Anti-PD-L1 monoclonal antibody was injected intaperitoneally on days 10, 14, 18, and 22 after tumor inoculation. ELANE or PMSF-ELANE were delivered intra-tumorally when tumors reached ~80 mm³ (~ 14 days post cancer cell injection). (FIG. 20A) Tumor volume was measured by calipers. (FIG. 20B) Kaplan-Meier curve was plotted and the logrank test (Mentel-Cox method) was used for mouse survival analysis. End point of survival is defined as tumor volume >1000 mm³. *, p<0.05, Student's t-test.

Porcine pancrease protease (PPE) showed less susceptibility to alpha 1 anti-trypsin (A1AT) or serum blocking. Elastase activity for purified native ELANE or purified native PPE at various dose were measured. It's corresponding killing ability was also tested on MDA-MB-231 cancer cells. Killing was assessed 6 hrs after treatment by Calcein AM staining. Purified native ELANE (40 nM) or purified native PPE (80 nM) was incubated with different concentration of A1AT for 15 mins, followed by elastase activity test and killing capability to MDA-MB-231. Killing was assessed 6 hrs after treatment by Calcein AM staining. Purified native ELANE (40 nM) or purified native PPE (80 nM) was incubated with different concentration of fetal bovine serum (FBS) for 15 mins, followed by elastase activity test and killing capability to MDA-MB-231. Killing was assessed 6 hrs after treatment by Calcein AM staining.

The invention claimed is:

1. A method for killing a cancer cell by CD95 degradation comprising administering to a patient that has cancer an effective amount of a serine protease that cleaves CD95, wherein the cancer expresses CD95, and wherein the serine protease comprises:

a pancreatic porcine elastase (pELA1) polypeptide that is 96% to 100% identical to SEQ ID NO: 6; or a pELA1 polypeptide having 225 to 250 contiguous acids of pELA1 that is 98% to 100% identical to SEQ ID NO:6 (pELA1).

2. The method of claim 1, wherein the serine protease is a component in a fusion protein.

3. The method of claim 1, wherein the serine protease is administered intratumorally.

4. The method of claim 1, wherein the cancer cell is a bladder, blood, bone, bone marrow, brain/nervous system, breast, colorectal, esophageal, gastrointestinal, head, kidney, liver, lung, nasopharynx, neck, ovarian, pancreatic, prostate, skin, stomach, testicular, tongue, or uterine cancer cell.

5. The method of any one of claims 1, 1, or 3-4, further comprising administering a second anticancer therapy, wherein the second anticancer therapy is a chemotherapy, radiotherapy, immunotherapy, targeted therapy, or anti-hormonal therapy.

6. The method of claim 1, wherein the pELA1 polypeptide is coupled to a nanoparticle.

7. The method of claim 1, wherein the polypeptide starts from amino acid 27 and ends at amino acid 266 of SEQ ID NO:6 (pELA1).

* * * * *